US007297336B2

(12) United States Patent
Kerschbaumer et al.

(10) Patent No.: US 7,297,336 B2
(45) Date of Patent: Nov. 20, 2007

(54) FACTOR IXA SPECIFIC ANTIBODIES DISPLAYING FACTOR VIIIA LIKE ACTIVITY

(75) Inventors: Randolf Kerschbaumer, Vienna (AT); Friedrich Scheiflinger, Vienna (AT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 308 days.

(21) Appl. No.: 10/661,366

(22) Filed: Sep. 12, 2003

(65) Prior Publication Data

US 2005/0058640 A1    Mar. 17, 2005

(51) Int. Cl.
*A61K 39/395* (2006.01)
(52) U.S. Cl. .............................. 424/146.1; 424/141.1; 424/145.1; 424/135.1; 424/185.1; 424/178.1; 424/133.1; 530/387.3; 530/388.25; 530/388.26
(58) Field of Classification Search ...................... None
See application file for complete search history.

(56) References Cited

U.S. PATENT DOCUMENTS

| 4,395,396 A | 7/1983 | Eibl et al. |
| 4,873,316 A | 10/1989 | Meade et al. |
| 5,932,706 A | 8/1999 | Mertens et al. |
| 6,391,299 B1 | 5/2002 | Blackburn et al. |
| 6,632,927 B2 | 10/2003 | Adair et al. |

FOREIGN PATENT DOCUMENTS

| WO | WO 95/13300 A1 | 5/1995 |
| WO | WO 97/26010 A1 | 7/1997 |
| WO | WO 9813067 A1 * | 4/1998 |
| WO | WO 99/01476 A1 | 1/1999 |
| WO | WO 02/081496 A2 * | 10/2002 |
| WO | WO 02/090566 A2 * | 11/2002 |

OTHER PUBLICATIONS

Janeway et al. Immunobiology, third edition, 1997, Garland Press, pp. 3:7 to 3:11.*
Watson et al., Molecular Biology of the Gene, fourth edition, 1987, The Benjamin/Cummings Publishing Company, Inc., p. 840.*
Ames, R.S. et al., "Conversion of Murine Fabs Isolated From a Combinatorial Phage Display Library to Full Length immunoglobulins", *J. immunol. Methods*, 1995, pp. 177-186.
Bajaj, S. P. et al., A Monoclonal Antibody to Factor IX That Inhibits the Factor V111: Ca Potentiation of FactorX Activation, The Journal of Biological Chemistry, 260(21), pp. 11574-11580 (1985).
Bessos, H., et al., The Characterization of a Panel of Monoclonal Antibodies to Human Coagulation Factor IX, Thrombosis Research, 40, pp. 863-867 (1985).
Cao, Y. et al., Bispecific Antibodies as Novel Bioconjugates, Bioconjugate Chemistry, 9(6), pp. 635-644 (1998).
Cohen, F.E., et al., The Combinatorial Approach, Protein Structure Prediction-A Practical Approach (Ed. M.J.E. Stemberg), Oxford University Press, Ch. 9, pp. 207-227 (1996).

Engelhardt, 0., et al., *Two-Step Cloning of Antibody Variable Domains in a Phage Display Vector*, Biotechniques, 17, p. 44-46 (1994).
Esser, C., et al., Immunoglobulin Class Switching: Molecular and Cellular Analysis, Annu. Rev. Immunol., 8, pp. 717-735 (1990).
Evan, G. I., et al., Isolation of Monoclonal Antibodies Specific for Human c-myc Proto-Oncogene Product, Mol. Cell. Biol., 5(12), p. 3610-3616 (1985).
Fay, P.J., et al., *Factor VIIIa A2 Subunit Residues 558-565 Represent a Factor IXa Interactive Site*, Journal of Biological Chemistry, 269(32), p. 20522-20527 (1994).
Frazier, D., et al., Mapping of Monoclonal Antibodies to Human Factor IX, Blood, 74(3), p. 971-977 (1989).
Gao, C., et al., Making Artificial Antibodies: A Format for Phage Display of Combinatorial Heterodimeric Arrays, Proc. Natl. Acad. Sci., 96, p. 6025-6030 (1999).
Grassy, G., et al., Computer-Assisted Rational Design of Immunosuppressive Compounds, Nature Biotechnology, 16, p. 748-752 (1998).
Greer, J., et al., Application of the Three-Dimensional Structures of Protein Target Molecules in Structure-Based Drug Design, Journal of Medicinal Chemistry, 37(8), p. 1035-1054 (1994).
Harlow, E., et al., 2. Antibody Molecules, Antibodies-A Laboratory Manual; pp. 7-22 (1988).
Harlow, E., et al., 3. Antibody-Antigen Interactions, Antibodies-A Laboratory Manual; p. 23-35(1988).
Harlow, E., et al., 6. Monoclonal Antibodies, Antibodies-A Laboratory Manual; p. 139-243(1988).
Hochuli, E., et al., Genetic Approach to Facilitate Purification of Recombinant Proteins with a Novel Metal Chelate Adsorbent, Biotechnology, 6, p. 1321-1325 (1988).
Huston, J. S., et al., Medical Applications of Single-Chain Antibodies, Intern. Rev. Immunol., 10, p. 195-217 (1993).
Jones, D.T., et al., Protein Folds and Their Recognition from Sequence, Protein Structure Prediction—A Practical Approach (Ed. M.J.E. Stemberg), Oxford University Press, Ch. 8,. p. 174-206 (1996).
Jones, P.T., et al., Replacing the Complementarity-Determining Regions in a Human Antibody with Those from a Mouse, Nature, 321, p. 522-525 (1986).
Jorquera, J. I., et al., Synthetic Peptides Derived from Residues 698-710 of Factor VIII Inhibit Factor. IXa Activity, Circulation, 86, Abstract No. 2725, p. 1-685 (1992).
Karpen, M.E., et al., Modelling Protein Conformation by Molecular Mechanics and Dynamics, Protein Structure Prediction—A Practical Approach (Ed. M.J.E. Stemberg), Oxford University Press, Ch. 10, p. 229-261 (1996).

(Continued)

*Primary Examiner*—G. R. Ewoldt
*Assistant Examiner*—Michael Szperk
(74) *Attorney, Agent, or Firm*—Townsend and Townsend and Crew LLP

(57) ABSTRACT

Ligands such as antibodies that can bind factor IX/factor IXa and increase the procoagulant activity of factor IXa (FIXa), pharmaceutical compositions containing such ligands, methods for treating patients afflicted with blood coagulation with such ligands, and a nucleic acid that encodes, or a cell that expresses such ligands, are provided.

13 Claims, 11 Drawing Sheets

OTHER PUBLICATIONS

Kemp, D.S., Peptidomimetics and the Template Approach to Nucleation of B-sheets and a helices in Peptides, TIBTECH, 8, p. 249-255 (1990).

Kerschbaumer, R.J. et al., Single-Chain Fv Fusion Proteins Suitable as Coating and Detecting Reagents in a Double Antibody Sandwich Enzyme-Linked Immunosorbent Assay, Analytical Biochemistry, 249, p. 219-227 (1997).

Kerschbaumer, R.J., et al, pDAP2: A Vector for Construction of Alkaline Phosphatase Fusion Proteins, immunotechnology, 2, p. 145-150 (1996).

Lane, R. D., A Short-Duration Polyethylene Glycol Fusion Technique for Increasing Production of Monoclonal Antibody-Secreting Hybridomas, Journal of Immunological Methods, 81, p. 223-227 (1985).

Lenting, P.J., et al., The Sequence Gluf°f'-Lys'd'd of Human Blood Coagulation Factor VIII Comprises a Binding Site for Activated Factor IX, Journal of Biological Chemistry, 271(4), p. 1935-1940 (1996).

Liles, D. K., et al, The Factor VIII Peptide Consisting of Amino Acids 698 to 712 Enhances Factor IXa Cleavage of FactorX, Blood, 90(1), Abstract No. 2054, p. 463a (1997).

Lin, H-F., et al, A Coagulation Factor IX-Deficient Mouse Model for Human Hemophilia B, Blood, 90(10), p. 3962-3966 (1997).

Malik, P., et al., Multiple Display of Foreign Peptide Epitopes on Filamentous Bacteriophage Virions, Phage Display of Peptides and Proteins (Ed. B. K. Kay et al.), Academic Press, p. 127-139 (1996).

Mann, K.G., et al., Surface-Dependent Reactions of the Vitamin K-Dependent Enzyme Complexes, Blood, 76(1), p. 1-16 (1990).

Mikaelsson, M., et al., Standardization of VIII:C Assays: A Manufacturer's View, Scandinavian Journal of Haematoloqy (Ed. Nilsson et al.), 33, p. 79-86 (1984).

Nilsson, I.M. et al., Induction of Split Tolerance and Clinical Cure in High-Responding Hemophiliacs with Factor IX Antibodies, Proc. Natl. Acad. Sci. USA, 83, p. 9169-9173 (1986).

Panka et al. "Variable region framework differences result in decreased or increased affinity of variant anti-digoxin antibodies." *Proc. Natl. Acad. Sci. USA*, May 1988, pp. 3080-3084, vol. 85, No. 9.

Persic, L., et al., An Integrated Vector System For The Eukaryotic Expression of Antibodies or Their Fragments After Selection From Phase Display Libraries, Gene, p. 9-18 (1997).

Pluckthun, A., et al., New Protein Engineering Approaches to Multivalent and Bispecific Antibody Fragments, Immunotechnology, 3, p. 83-105 (1997).

Raag, R., et al., Single-Chain Fvs, FASEB Journal, 9(1), pp. 73-80 (1995).

Rees, A.R., et al., Antibody Combining Sites: Structure and Prediction, Protein Structure Prediction—A Practical Approach (Ed. M.J.E. Sternberg), Oxford University Press, Ch. 7, p. 141-172 (1996).

Roitt, LM., et al., Molecules which Recognize Antigen, Immunology, 2nd Edition, p. 5.1-5.11(1989).

Rudikoff et al. "Single amino acid substitution altering antigen-binding specificity." *Proc. Natl. Acad. Sci. USA*, 1982, pp. 1979-1983, vol. 79, No. 6.

Sadler, J.E., et al., Hemophilia A, Hemophilia B, and von Willebrand's Disease, The Molecular Basis of Blood Diseases (Ed. G. Stamatoyannopoulos et al.), p. 575-630 (1987).

Vaughan, T.J., et al., Human Antibodies By Design, Nature Biotechnology, p. 535-539(1998).

Winter, G., et al., Making Antibodies by Phage Display Technology, Annu. Rev. Immunol., 12, p. 433-455 (1994).

Zhong, D., et al., Some Human Inhibitor Antibodies Interfere with Factor VIII Binding to Factor IX, Blood, 92(1), p. 136-142 (1998).

* cited by examiner

```
       Q   V   Q   M   Q   Q   S   G   A   E   L   V   K   P   G
  1   CAG GTT CAG ATG CAG CAG TCT GGG GCT GAA CTG GTA AAG CCT GGG

A   S   V   K   L   S   C   K   A   S   G   Y   T   F   T
 46   GCT TCA GTG AAG TTG TCC TGC AAG GCT TCT GGC TAC ACC TTC ACA

S   Q   D   I   N   W   V   R   Q   R   P   E   Q   G   L
 91   AGC CAA GAT ATA AAC TGG GTG AGG CAG AGG CCT GAA CAG GGA CTT

E   W   I   G   W   I   F   P   G   D   G   S   T   K   Y
136   GAG TGG ATT GGA TGG ATT TTT CCT GGA GAT GGT AGT ACA AAG TAC

N   E   K   L   K   G   K   A   T   L   T   T   D   K   S
181   AAT GAG AAG TTG AAG GGC AAG GCG ACA CTG ACT ACA GAC AAA TCC

S   S   T   A   F   M   Q   L   S   R   L   T   S   E   D
226   TCC AGC ACA GCC TTC ATG CAG CTC AGC AGG CTG ACA TCT GAG GAC

S   A   V   Y   F   C   A   R   S   A   Y   Y   R   Y   D
271   TCT GCT GTC TAT TTC TGT GCA AGA TCC GCC TAC TAT CGG TAC GAC

G   S   Y   Y   Y   A   M   D   Y   W   G   Q   G   T   S
316   GGG TCC TAT TAC TAT GCT ATG GAC TAC TGG GGT CAA GGA ACC TCA

V   T   V   S   S
361   GTC ACC GTC TCC TCA
```

FIGURE 6

|     |     |     |     |     |     |     |     |     |     |     |     |     |     |     |
| --- | --- | --- | --- | --- | --- | --- | --- | --- | --- | --- | --- | --- | --- | --- |
|     | Q   | I   | V   | L   | T   | Q   | S   | P   | A   | I   | M   | S   | A   | S   | L   |
| 1   | CAA | ATT | GTT | CTC | ACC | CAG | TCT | CCA | GCA | ATC | ATG | TCT | GCA | TCT | CTA |
|     | G   | E   | E   | I   | T   | L   | T   | C   | S   | A   | S   | S   | S   | V   | S   |
| 46  | GGG | GAG | GAG | ATC | ACC | CTA | ACC | TGC | AGT | GCC | AGC | TCA | AGT | GTA | AGT |
|     | Y   | M   | L   | W   | Y   | Q   | Q   | K   | S   | G   | T   | S   | P   | K   | L   |
| 91  | TAC | ATG | CTC | TGG | TAC | CAG | CAG | AAG | TCA | GGC | ACT | TCT | CCC | AAA | CTC |
|     | L   | I   | Y   | T   | T   | S   | N   | L   | A   | S   | G   | V   | P   | S   | R   |
| 136 | TTG | ATT | TAT | ACC | ACA | TCC | AAC | CTG | GCT | TCT | GGA | GTC | CCT | TCT | CGC |
|     | F   | S   | G   | T   | G   | S   | G   | T   | F   | Y   | S   | L   | T   | I   | S   |
| 181 | TTC | AGT | GGC | ACT | GGG | TCT | GGG | ACC | TTT | TAT | TCT | CTC | ACA | ATC | AGC |
|     | S   | V   | E   | A   | E   | D   | A   | A   | D   | Y   | Y   | C   | H   | Q   | W   |
| 226 | AGT | GTG | GAG | GCT | GAA | GAT | GCT | GCC | GAT | TAT | TAC | TGC | CAT | CAG | TGG |
|     | S   | S   | Y   | P   | R   | T   | F   | G   | G   | G   | T   | K   | L   | E   | I   |
| 271 | AGT | AGT | TAT | CCA | CGG | ACG | TTC | GGT | GGA | GGC | ACC | AAG | CTG | GAA | ATC |
|     | K   | R   |     |     |     |     |     |     |     |     |     |     |     |     |     |
| 316 | AAA | AGG |     |     |     |     |     |     |     |     |     |     |     |     |     |

FIGURE 7

CDR Loops of antibody 224F3:

Light chain

L1 (SEQ ID NO:3):  $Ser_{24}$  $Ala_{25}$  $Ser_{26}$  $Ser_{27}$  $Ser_{28}$  $Val_{29}$  $Ser_{30}$  $Tyr_{31}$  $Met_{32}$  $Leu_{33}$

L2 (SEQ ID NO:4):  $Thr_{49}$  $Thr_{50}$  $Ser_{51}$  $Asn_{52}$  $Leu_{53}$  $Ala_{54}$  $Ser_{55}$

L3 (SEQ ID NO:5):  $His_{88}$  $Gln_{89}$  $Trp_{90}$  $Ser_{91}$  $Ser_{92}$  $Tyr_{93}$  $Pro_{94}$  $Arg_{95}$  $Thr_{96}$

Heavy chain

H1 (SEQ ID NO:6):  $Gly_{134}$  $Tyr_{135}$  $Thr_{136}$  $Phe_{137}$  $Thr_{138}$  $Ser_{139}$  $Gln_{140}$  $Asp_{141}$  $Ile_{142}$  $Asn_{143}$

H2 (SEQ ID NO:7):  $Trp_{158}$  $Ile_{159}$  $Phe_{160}$  $Pro_{161}$  $Gly_{162}$  $Asp_{163}$  $Gly_{164}$  $Ser_{165}$  $Thr_{166}$  $Lys_{167}$

H3 (SEQ ID NO:8):  $Ser_{207}$  $Ala_{208}$  $Tyr_{209}$  $Tyr_{210}$  $Arg_{211}$  $Tyr_{212}$  $Asp_{213}$  $Gly_{214}$  $Ser_{215}$  $Tyr_{216}$  $Tyr_{217}$  $Tyr_{218}$  $Ala_{219}$  $Met_{220}$  $Asp_{221}$  $Tyr_{222}$

FIGURE 8

SEQUENCE LISTING

```
<160> NUMBER OF SEQ ID NOS: 12

<210> SEQ ID NO 1
<211> LENGTH: 125
<212> TYPE: PRT
<213> ORGANISM: Mus musculus
<220> FEATURE:
<223> OTHER INFORMATION: mouse monoclonal antibody 224F3 variable heavy
      chain (V-H)

<400> SEQUENCE: 1

Gln Val Gln Met Gln Gln Ser Gly Ala Glu Leu Val Lys Pro Gly Ala
  1               5                  10                  15

Ser Val Lys Leu Ser Cys Lys Ala Ser Gly Tyr Thr Phe Thr Ser Gln
             20                  25                  30

Asp Ile Asn Trp Val Arg Gln Arg Pro Glu Gln Gly Leu Glu Trp Ile
         35                  40                  45

Gly Trp Ile Phe Pro Gly Asp Gly Ser Thr Lys Tyr Asn Glu Lys Leu
     50                  55                  60

Lys Gly Lys Ala Thr Leu Thr Thr Asp Lys Ser Ser Ser Thr Ala Phe
 65                  70                  75                  80

Met Gln Leu Ser Arg Leu Thr Ser Glu Asp Ser Ala Val Tyr Phe Cys
                 85                  90                  95

Ala Arg Ser Ala Tyr Tyr Arg Tyr Asp Gly Ser Tyr Tyr Tyr Ala Met
            100                 105                 110

Asp Tyr Trp Gly Gln Gly Thr Ser Val Thr Val Ser Ser
        115                 120                 125

<210> SEQ ID NO 2
<211> LENGTH: 107
<212> TYPE: PRT
<213> ORGANISM: Mus musculus
<220> FEATURE:
<223> OTHER INFORMATION: mouse monoclonal antibody 224F3 variable light
      chain (V-L)

<400> SEQUENCE: 2
```

-continued

```
Gln Ile Val Leu Thr Gln Ser Pro Ala Ile Met Ser Ala Ser Leu Gly
 1               5                  10                  15

Glu Glu Ile Thr Leu Thr Cys Ser Ala Ser Ser Ser Val Ser Tyr Met
                20                  25                  30

Leu Trp Tyr Gln Gln Lys Ser Gly Thr Ser Pro Lys Leu Leu Ile Tyr
            35                  40                  45

Thr Thr Ser Asn Leu Ala Ser Gly Val Pro Ser Arg Phe Ser Gly Thr
        50                  55                  60

Gly Ser Gly Thr Phe Tyr Ser Leu Thr Ile Ser Ser Val Glu Ala Glu
 65                  70                  75                  80

Asp Ala Ala Asp Tyr Tyr Cys His Gln Trp Ser Ser Tyr Pro Arg Thr
                85                  90                  95

Phe Gly Gly Gly Thr Lys Leu Glu Ile Lys Arg
            100                 105
```

<210> SEQ ID NO 3
<211> LENGTH: 10
<212> TYPE: PRT
<213> ORGANISM: Mus musculus
<220> FEATURE:
<223> OTHER INFORMATION: mouse monoclonal antibody 224F3 variable light
      chain (V-L) complement determining region (CDR)
      loop L1

<400> SEQUENCE: 3

```
Ser Ala Ser Ser Ser Val Ser Tyr Met Leu
 1               5                  10
```

<210> SEQ ID NO 4
<211> LENGTH: 7
<212> TYPE: PRT
<213> ORGANISM: Mus musculus
<220> FEATURE:
<223> OTHER INFORMATION: mouse monoclonal antibody 224F3 variable light
      chain (V-L) complement determining region (CDR)
      loop L2

<400> SEQUENCE: 4

```
Thr Thr Ser Asn Leu Ala Ser
 1               5
```

<210> SEQ ID NO 5
<211> LENGTH: 8
<212> TYPE: PRT
<213> ORGANISM: Mus musculus
<220> FEATURE:
<223> OTHER INFORMATION: mouse monoclonal antibody 224F3 variable light
      chain (V-L) complement determining region (CDR)
      loop L3

<400> SEQUENCE: 5

```
His Gln Trp Ser Ser Tyr Pro Arg
 1               5
```

<210> SEQ ID NO 6
<211> LENGTH: 10
<212> TYPE: PRT
<213> ORGANISM: Mus musculus
<220> FEATURE:
<223> OTHER INFORMATION: mouse monoclonal antibody 224F3 variable heavy
      chain (V-H) complement determining region (CDR)
      loop H1

<400> SEQUENCE: 6

Gly Tyr Thr Phe Thr Ser Gln Asp Ile Asn

<210> SEQ ID NO 7
<211> LENGTH: 10
<212> TYPE: PRT
<213> ORGANISM: Mus musculus
<220> FEATURE:
<223> OTHER INFORMATION: mouse monoclonal antibody 224F3 variable heavy
      chain (V-H) complement determining region (CDR)
      loop H2

<400> SEQUENCE: 7

Trp Ile Phe Pro Gly Asp Gly Ser Thr Lys
 1               5                  10

<210> SEQ ID NO 8
<211> LENGTH: 16
<212> TYPE: PRT
<213> ORGANISM: Mus musculus
<220> FEATURE:
<223> OTHER INFORMATION: mouse monoclonal antibody 224F3 variable heavy
      chain (V-H) complement determining region (CDR)
      loop H3

<400> SEQUENCE: 8

Ser Ala Tyr Tyr Arg Tyr Asp Gly Ser Tyr Tyr Tyr Ala Met Asp Tyr
 1               5                  10                  15

<210> SEQ ID NO 9
<211> LENGTH: 375
<212> TYPE: DNA
<213> ORGANISM: Mus musculus
<220> FEATURE:
<223> OTHER INFORMATION: mouse monoclonal antibody 224F3 variable heavy
      chain (V-H)

<400> SEQUENCE: 9
caggttcaga tgcagcagtc tggggctgaa ctggtaaagc ctggggcttc agtgaagttg      60
tcctgcaagg cttctggcta caccttcaca agccaagata taaactgggt gaggcagagg     120
cctgaacagg gacttgagtg gattggatgg attttccctg gagatggtag tacaaagtac     180
aatgagaagt tgaagggcaa ggcgacactg actacagaca atcctccag cacagccttc      240 atgcagctca gcaggctgac atctgaggac tctgctgtct atttctgtgc aagatccgcc     300
tactatcggt acgacgggtc ctattactat gctatggact actggggtca aggaacctca     360
gtcaccgtct cctca                                                       375

<210> SEQ ID NO 10
<211> LENGTH: 321
<212> TYPE: DNA
<213> ORGANISM: Mus musculus
<220> FEATURE:
<223> OTHER INFORMATION: mouse monoclonal antibody 224F3 variable light
      chain (V-L)

<400> SEQUENCE: 10
caaattgttc tcacccagtc tccagcaatc atgtctgcat ctctagggga ggagatcacc      60
ctaacctgca gtgccagctc aagtgtaagt tacatgctct ggtaccagca gaagtcaggc     120
acttctccca aactcttgat ttataccaca tccaacctgg cttctggagt cccttctcgc     180
ttcagtggca ctgggtctgg gacctttat tctctcacaa tcagcagtgt ggaggctgaa      240
gatgctgccg attattactg ccatcagtgg agtagttatc cacggacgtt cggtggaggc     300
accaagctgg aaatcaaaag g                                                321

```
<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:peptide
      linker

<400> SEQUENCE: 11

Gly Gly Gly Gly Ser
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:hexa-
      histidine tag

<400> SEQUENCE: 12

His His His His His His
 1               5
```

FACTOR IXA SPECIFIC ANTIBODIES DISPLAYING FACTOR VIIIA LIKE ACTIVITY

FIELD OF THE INVENTION

The invention relates to ligands that can bind to factor IX/factor IXa and activate the procoagulant activity of factor IXa (FIXa), derivatives of these ligands, pharmaceutical compositions containing such ligands, methods that involve administering such ligands to treat patients afflicted with blood coagulation disorders, nucleic acids encoding certain ligands that are proteins, and cells expressing such ligands.

BACKGROUND

One of the key events during normal haemostasis is the conversion of the zymogen factor X (FX) into its enzymatically active form FXa, a process which subsequently leads to prothrombin activation and clot formation. In vivo FX activation is initially achieved through the tissue factor/factor VIIa pathway. The tissue factor/factor VIIa complex is readily inhibited by the tissue factor pathway inhibitor. The activation of the major part of FX subsequently occurs via the intrinsic coagulation pathway and requires formation of the intrinsic factor X-activating complex. This complex consists of the coagulation factors Factor IXa (FIXa) and Factor VIIIa (F VIIIa) assembled on a phospholipid surface in the presence of $Ca^{2+}$ ions. The intrinsic factor X-activating complex produces FXa at a level that enables the formation of a stable clot.

FVIIIa functions as an activator of factor IXa (F IXa), which increases the rate of FXa formation approximately 200,000-fold (van Dieijen et al., (1981) J. Biol. Chem. 256:3433-3442). The exact mechanism by which FVIIIa enhances the catalytic activity of FIXa towards FX is still unknown. Natural occurring mutants, site-directed mutagenesis, as well as the analysis of similar cofactor/enzyme complexes, like the prothrombinase complex, suggest that there are at least two contact regions between FVIIIa and FIXa. Both regions play an important role in enhancing FIXa enzymatic activity. It is generally believed that FVIII has three functions within the intrinsic factor X-activating complex: (i) FVIII stabilizes a conformation of FIXa which has increased protease activity towards FX, (ii) FVIIIa acts as a receptor for FIXa on activated platelets which in vivo provide the procoagulant phospholipid surface and (iii) recent data indicates that FVIIIa orients the cleavage sites in FX towards the active site of FIXa.

The crucial role of FVIII in haemostasis is demonstrated by hemophilia A, a severe X-chromosome-linked recessive bleeding disorder, which is characterized by the absence of coagulation factor FVIII activity. Patients with haemophilia A are treated by administering FVIII to a patient via intravenous injection of either plasma-derived or recombinant FVIII. Although such methods are efficient, they suffer from several drawbacks. First, the relatively short half-life of FVIII means that it is necessary to administer high doses of FVIII two to three times a week. Second, FVIII production is very expensive; consequently, it is available primarily only in the industrialized world. Finally, approximately 30% of severely affected patients develop antibodies that inhibit FVIII activity ("hemophilia inhibitor patients" or simply "inhibitor patients"), which is a serious and life threatening complication.

In view of the key role that FVIII plays in haemostasis coupled with the foregoing shortcomings in delivering it to patients with blood coagulation disorders, there remains a significant need for compounds that have activities similar to FVIII but which overcome some of its limitations.

SUMMARY

The invention provides, in part, ligands that function as substitutes for factor VIIIa in the treatment of blood coagulation disorders (e.g., hemophilia and hemorrhagia diathesis). These ligands can thus bind to factor IXa and stimulate the procoagulant activity of factor IXa. Certain ligands can bind to factor IXa such that antibodies that inhibit Factor VIII do not adversely affect the procoagulant activity of factor IXa. One specific group of ligands that is provided: (i) bind to factor IX/factor IXa, thereby increasing the procoagulant activity of FIXa, and, (ii) contain at least one of the amino acid sequences as listed in SEQ ID NOs: 1 to 8. Other ligands are derivatives of these ligands. Some ligands are antibodies that comprise at least one amino acid sequence as listed in SEQ ID NOs:1-8 and competitively inhibit binding of a reference antibody capable of binding to Factor IX/IXa. Thus, certain antibodies include at least one amino acid sequence as listed in SEQ ID NOs:1-8, can bind to Factor IX/Factor IXa and can increase the procoagulation activity of FIXa.

Cells expressing such ligands and nucleic acids encoding these ligands are also provided, as are methods for producing such ligands and methods for using these cells or nucleic acids.

Pharmaceutical compositions for the treatment of blood coagulation disorders such as hemophilia A and hemorrhagia diathesis (e.g., in man) are also described herein. Certain pharmaceutical compositions contain, for example, one or more of the ligands that are disclosed herein and a pharmaceutical acceptable carrier and/or diluent.

BRIEF DESCRIPTION OF THE DRAWINGS

FIG. 2 shows the effect of procoagulant antibody 224F3 on FIXa-catalyzed FX activation.

FIGS. 6 and 7 show the sequence of the variable heavy chain, $V_H$, (amino acid=SEQ ID NO:1; nucleotide=SEQ ID NO:9) and the variable light chain, $V_L$, (amino acid=SEQ ID NO:2; nucleotide=SEQ ID NO:10) of the antibody 224F3.

FIG. 8 shows the sequences of the CDR (complement determining regions) L1 to L3 (SEQ ID NOs: 3 to 5) and H1 to H3 (SEQ ID NOs: 6 to 8) of antibody 224F3. The indices at each amino acid residue identify the position of each amino acid residue in the respective polypeptide chain of the antibody 224F3. The numbers will vary with the framework into which the sequences L1 to L3 and H1 to H3, namely SEQ ID NO: 3 to 8, are introduced. Accordingly, the indices do not form a part of the sequences according to SEQ ID NO: 3 to 8. Thus, the indices shall not considered to be limiting for the sequences.

DETAILED DESCRIPTION

1. Definitions

Figure 1:
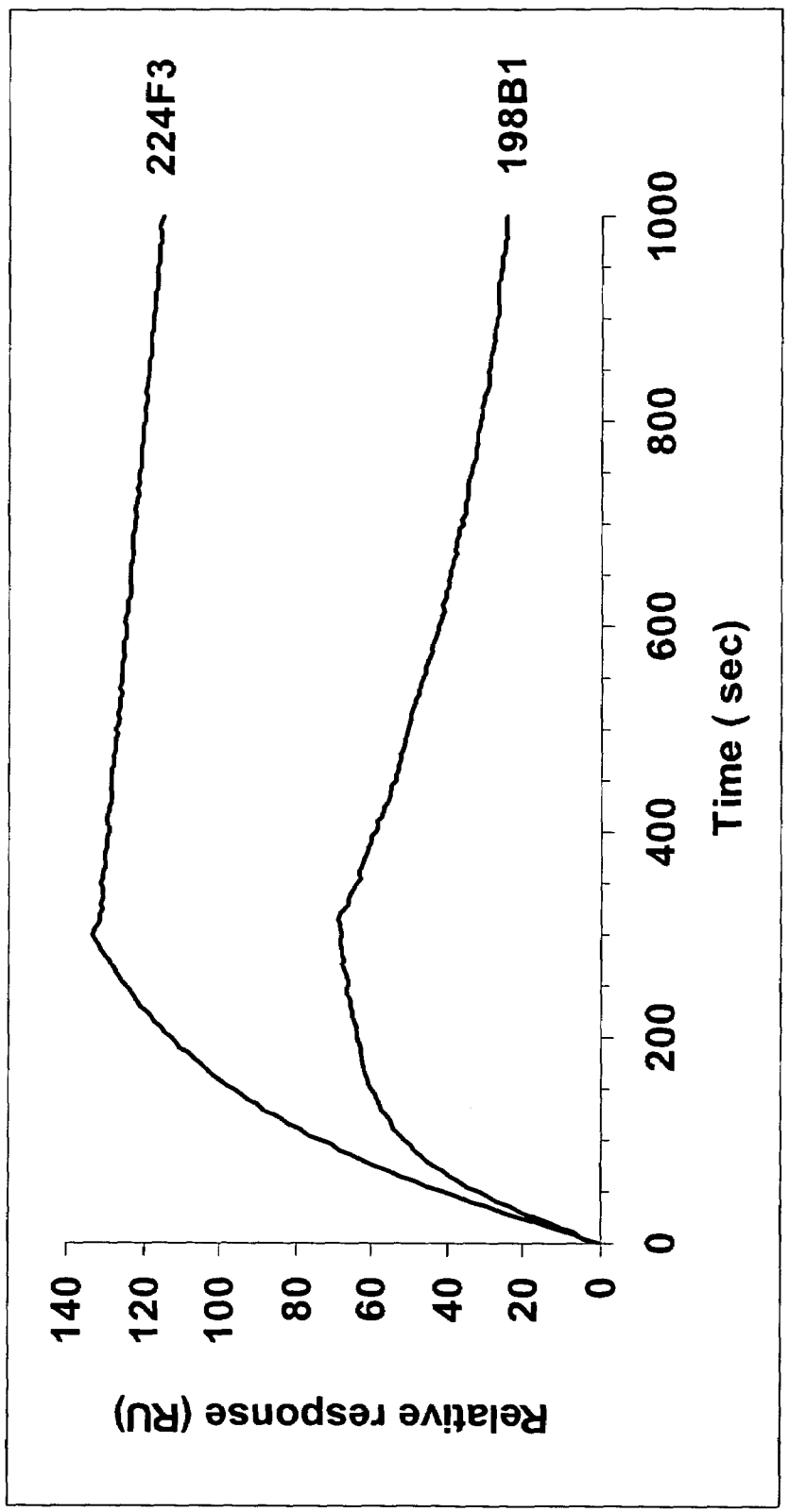
FIG. 1 shows the kinetics of the interaction of FIXa and the antibodies 198B1 (see WO 01/19992) and 224F3 in the presence of 5 mM $CaCl_2$ as measured by Surface Plasmon Resonance (SPR) technology using a BIACORE 300 Instrument (Biacore AG, Uppsala, Sweden). More specifically, this figure shows the binding of 5.56 nM FIXa to these two different monoclonal antibodies (Mabs) captured by anti-mouse Fcγ (RAMFc) in the presence of 5 mM $CaCl_2$. During the analysis, 5.56 nM FIXa was injected, the association was followed for 5 minutes, and the dissociation monitored for 12 minutes. Time in seconds is shown on the abscissa; the relative response in arbitrary units is shown on the ordinate.

Factor VIII as used herein has its general meaning in the art and refers to various polypeptides arising from a single gene product (see, e.g., Andersson et al., Proc. Natl. Acad. Sci. USA, 83, 2979-2983, May 1986; Gitschier, J. et al. (1984) Nature 312, 326-330; Wood, W. I. et al. (1984) Nature 312, 330-337; Vehar, G. A. et al. (1984) Nature 312, 337-342; and Toole, J. J. et al. (1984) Nature 312, 342-347), whether derived from blood plasma or produced through the use of synthetic or recombinant DNA techniques. Factor VIII naturally exists in several forms, as the full-length protein and smaller forms that are formed via cleavage of the full-length form. Full length Factor VIII is described, for example, in U.S. Pat. Nos. 5,633,150 and 4,757,006. Factor VIII mRNA encodes a precursor protein of 2351 amino acids including a 19 amino acid signal peptide; thus the mature Factor VIII protein is 2332 amino acids long. The amino acid sequence predicted a domain structure consisting of a triplicated A domain, a unique B domain and a duplicated C domain arranged in the order A1:A2:B:A3:C1:C2. During coagulation, the B domain is removed by thrombin activation of the molecule. Commercially available examples of therapeutic preparations containing recombinant Factor VIII include those sold under the trade names of HEMOFIL M™, ADVATE™ and RECOMBINATE™ (available from Baxter Healthcare Corporation, Deerfield, Ill., U.S.A.) and KOGENATE (available from Bayer, North Carolina).

The term Factor VIII also includes variant forms, including proteins with substitutions, additions or deletions that retain procoagulant activity. Certain molecules that are included within the term Factor VIII lack a domain from full-length Factor VIII. For example, Factor VIII lacking the B domain (r-VIII SQ) is produced by Wyeth, Massachusetts (see, e.g., Berntorp, E. (1997) Thrombosis and Haemostasis 78, 256-260; see also EP-A-0506757). This particular protein consists of a 90 kDa heavy chain (domains A1:A2) and the 80 kDa light chain (domains A3: C1:C2), which are connected by a linker peptide. The term Factor VIII includes molecules having substantial sequence identity to naturally occurring Factor VIII that have Factor VIII activity.

Factor IX as used herein has its general meaning in the art and includes naturally occurring forms and variants thereof produced via synthetic, recombinant or other means that retain Factor IX/IXa activity. The cDNA coding for human factor IX has been described by various groups (see, e.g., Choo et al., Nature 299:178-180 (1982); Fair et al., Blood 64:194-204 (1984); and Kurachi et al., Proc. Nat. Acad. Sci., U.S.A. 79:6461-6464 (1982)). Methods of producing factor IX by recombinant DNA techniques are described in U.S. Pat. No. 4,770,999. The term includes proteins with substitutions, additions or deletions relative to naturally occurring Factor IX that retain the ability to activate Factor X. For example, a Factor IX protein with a substitution is described in U.S. Pat. No. 6,599,724. The term can also include various processed forms such as Factor IXaα and Factor IXaβ. For an overview of Factor IX, see, e.g., Limentani, S. A., et al., "The Biochemistry of Factor IX," in Hemostasis and Thrombosis: Basic Principles and Clinical Practice, 3rd ed. (Colman, R. W., et al., Eds) chap. 5, J.B. Lippincott Co., Philadelphia, 1994.

Procoagulant activity as used herein has its general meaning in the art and generally refers to an activity that promotes clot formation. This activity can be monitored with blood samples or other assays known in art (see, e.g., the assays described in the examples). The antibodies disclosed herein have procoagulant activity in that they can interact with Factor IXa so as to increase the rate at which Factor IXa converts Factor X to Factor Xa. Increases in procoagulation activity can be measured using assays such as described in the examples. Assays for an increase in activity are generally compared with respect to a control or baseline level (e.g., a sample from a hemophilia patient that lacks Factor VIII).

As used herein, "antibody" is meant to refer generally to an immunoglobulin molecule that is immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability [e.g., Fab', F(ab')$_2$, Fab, Fv and rIgG. See, e.g., Pierce Catalog and Handbook, 1994-1995 (Pierce Chemical Co., Rockford, Ill.); Kuby, J., *Immunology*, 3$^{rd}$ Ed., W.H. Freeman & Co., New York (1998)]. The term also encompasses recombinant single chain Fv fragments (scFv). The term further includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al., 1993, supra, Gruber et al. (1994) *J. Immunol.* :5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues which are found neither in the recipient antibody nor in the imported CDR or framework sequences. In general, a humanized antibody comprises substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)). Humanization can be performed, for example, by following the method of Winter and co-workers [(see, e.g., Jones et al., *Nature* 321:522-525 (1986); Riechmann et al., *Nature* 332:323-327 (1988); Verhoeyen et al., *Science* 239:1534-1536 (1988)], and by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps. Preferably, identity exists over a region that is at least about 5, 6, 7, 8 or 9 amino acids or nucleotides in length, or more preferably over a region that is 10, 15, 20, 25, 30, 40, 50, 60, 70, 80, 90 or 100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150 or 170.

A "host cell" is a naturally occurring cell or a transformed cell that contains an expression vector and supports the replication or expression of the expression vector. Host cells include, for example, cultured cells, explants and cells in vivo. Host cells can be prokaryotic cells such as E. coli, or eukaryotic cells such as yeast, insect, amphibian, or mammalian cells such as CHO and HeLa.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. A ligand (e.g., an antibody) that specifically binds to a protein generally has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

The terms "isolated," "purified," or "biologically pure" refer to material (e.g., an antibody) that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, $^3H$, $^{14}C$, $^{32}P$, $^{35}S$, or $^{125}I$.

II. Ligands, Including Antibodies

A. Structure and Activity

Disclosed herein are ligands that function as substitutes or complements for FVIIIa in activating FIXa. Such ligands have a number of utilities, including, use directly or as part of a pharmaceutical composition to treat individuals with various blood coagulation disorders and in the purification and detection of FIX/FIXa. Certain of the ligands that are provided were surprisingly found to have increased affinity for FIX/FIXa that bind FIX/FIXa (see, e.g., Examples 4 and 5 infra) and to increase the procoagulation activity of FIXa (see, e.g., Examples 6 and 7 below) as compared to other antibodies.

As used herein, the term "ligand" generally refers to:
1) a compound (a) that binds in vitro and/or in vivo to factor IX/factor IXa (preferably of human origin), (b) that activates the procoagulant activity of FIXa by forming a complex with FIXa, and (c) contains at least one of the amino acid sequences as listed in SEQ ID NOs: 1 to 8; and
2) derivatives of such compounds.

SEQ ID NOs: 1 and 2 are peptide sequences from the VH and the VL region, respectively, of antibody 224F3 (see FIGS. 6 and 7). SEQ ID NO: 3 to 8 are peptide sequences from the CDR sequences of the light chain, L1 to L3, and the heavy chain, H1 to H3, respectively, of antibody 224F3 (see FIG. 8).

The term "derivative" as used herein generally refers to a compound with characteristics (a) and (b) above, and that either (i) contains at least one of the amino acid sequences SEQ ID Nos: 1 to 8 wherein, all together, at most 25% of the number of the amino acid residues of the corresponding sequence are either substituted or deleted, or wherein any other number of amino acid residues of the corresponding sequence is substituted or deleted, or wherein one or more amino acids have been inserted into anyone of SEQ ID Nos: 1 to 8, so that the specific function of the ligand is retained or even improved, or (ii) does not fulfill the definition of item (i) but also exhibits the specific function of the ligand (e.g. a peptidomimetic compounds of proteinaceous or non-proteinaceous origin; see Kemp D S, Trends Biotechnol., 1990, pp. 249-255). Certain derivatives that are proteins (e.g., antibodies) include protein segments that have amino acid sequences substantially identical to one or more amino acid sequences as listed in SEQ ID NOs:1-8.

The term "specific function" of the ligands is defined as a ratio of more than 5:1, preferably more than 6:1, more preferably more than 6.5:1, or most preferably more than 6.8:1 of the catalytic efficiency in terms of the Michaelis-Menten kinetics ($k_{cat}/K_M$) of FIXa in the presence of the ligand in relation to the absence of the ligand and any other effector (for details see below).

Certain ligands are polypeptides, such as antibodies. In general, the antibodies that are provided recognize the same epitope as the complementary determining regions (CDR1, CDR2 and CDR3) that are listed in SEQ ID NOs:3-8. The ability of a particular antibody to recognize the same epitope as another antibody can be determined by the ability of one antibody to competitively inhibit binding of a second antibody (e.g., reference antibody) to the antigen (e.g., Factor IX or IXa). A number of competitive binding assays can be used to measure competition between two antibodies to the same antigen. On such assay is a Biacore assay (see, e.g., Example 5). Various immunoassays known in the art can also be used. For example, antibodies can be differentiated by the epitope to which they bind using a sandwich ELISA assay. This is carried out by using a capture antibody to coat the surface of a well. A subsaturating concentration of tagged-antigen is then added to the capture surface. This protein will be bound to the antibody through a specific antibody:epitope interaction. After washing, a second antibody, which has been covalently linked to a detectable moiety (e.g., HRP, with the labeled antibody being defined as the detection antibody) is added to the ELISA. If this antibody recognizes the same epitope as the capture antibody, it will be unable to bind to the target protein, as that particular epitope is no longer be available for binding. If, however, this second antibody recognizes a different epitope on the target protein, it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is generally considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Certain of the antibodies that are provided have one or more polypeptide chains, wherein at least one polypeptide chain comprises at least 3 loops or complement determining regions (i.e., CDR1, CDR2 and CDR3). One or more of these CDRs in turn comprise a sequence as listed in SEQ ID NOs: 3 to 8. In some antibodies, the CDRs are embedded in 4 framework region. The definition of the CDRs is in accordance with the Chothia numbering scheme (see, e.g., Al-Lazikani B., Lesk A. M. and Chothia C. 1997. *Standard conformations for the canonical structures of immunoglobulins*. J Mol Biol 273:927-948, the disclosure of which is incorporated herein by reference in its entirety for all purposes). Other ligands are derivatives of such antibodies. One or more (in some instances all) of the CDRs in these derivatives are substantially identical in amino acid sequence with the sequences listed in SEQ ID NOs:1-8.

Thus, some antibodies that are provided include at least three CDRs (CDR1, CDR2 and CDR3) that are embedded in four framework regions, wherein one or more of the at least three CDRs comprise an amino acid sequence as listed in SEQ ID NOs: 3 to 8. Other antibodies include one or more CDR3 segments, each CDR3 comprising an amino acid sequence selected from the group consisting of SEQ ID NOs: 5 and 8. In still other antibodies, CDR1, CDR2 and CDR3 each comprise an amino acid sequence selected from the group consisting of SEQ ID NOs: 3-5 or an amino acid sequence selected from the group consisting of SEQ ID NOs: 6-8. Certain other antibodies include one or both of the VH and VL regions as listed in SEQ ID NOs:1-2. Derivatives of these particular antibodies that have substantial sequence identity with SEQ ID NOs:1-8 are also included.

Some of the antibodies that are provided are polyclonal antibodies, whereas others are monoclonal. Other polypeptides that are provided are obtained via recombinant gene technology ("recombinant antibody"). Accordingly, some ligands comprise human and animal monoclonal antibodies or fragments thereof or, single chain antibodies and fragments thereof (including miniantibodies, bi-specific, diabodies, triabodies, or dimers, oligo- or multimers thereof).

Some ligands comprise proteins produced by expression of an altered, immunoglobulin-encoding region in a host cell. One example of ligands of this type are "technically modified antibodies." Antibodies in this class include, for instance, synthetic antibodies, chimeric or humanized antibodies, or mixtures thereof, or antibody fragments that partially or completely lack the constant region, (e.g., Fv, Fab, Fab' or F(ab)'$_2$). In technically modified antibodies, a part or parts of the light and/or heavy chain can be substituted. Such molecules can comprise antibodies consisting of a humanized heavy chain and an unmodified light chain (or chimeric light chain), or vice versa (for the term "humanized" see below). The terms Fv, Fc, Fd, Fab, Fab' or F(ab)$_2$ have their usual meaning in the art (see, e.g., Harlow E. and Lane D., in "Antibodies, A Laboratory Manual", Cold Spring Harbor Laboratory, 1988).

Certain ligands include Fab fragments or F(ab)$_2$ fragments that are derived from monoclonal antibodies (mAb) directed against factor IX/factor IXa, and that cause an increase of the procoagulant activity of factor IXa.

Some ligands are humanized antibodies that comprise CDRs from murine monoclonal antibodies that have been inserted in the heterologous framework regions of selected human antibody sequences. The framework regions comprise regions that are involved in the display of the CDR.

The constant regions, if present in the ligand, are typically selected from the human immunoglobulin classes and isotypes, such as IgG (subtypes 1 to 4), IgM, IgA and IgE. In the course of the immune response, a class switch of the immunoglobulins can occur (e.g., in a switch from IgM to IgG, the constant regions are exchanged from µ to γ). A class switch can also be caused in a directed manner by means of genetic engineering methods ("directed class switch recombination"), as is known from the prior art (see e.g., Esser C. and Radbruch A., Annu. Rev. Immunol., 1990, Vol. 8, pp. 717-735). Of course, in humanized antibodies, other sequences that are involved in the binding of the antibody to other cellular molecules like the constant regions are usually human, too.

In certain ligands, the variable regions in the human light and heavy chains are technically altered by exchanging 1, 2, 3, 4, 5 or 6 CDR with CDRs of murine origin, especially those CDRs listed in SEQ. ID. NOs. 3 to 8, or derivatives thereof. All six CDRs, or varying combinations of less than six CDRs, can be used.

A fully humanized antibody has the framework regions of a human antibody and CDRs of murine origin. This antibody behaves in terms of the antigenic response as a human antibody and comprises the combination and characteristics necessary for a therapeutic application, e.g., the treatment of coagulation disorders in patients such as factor VIII inhibitor patients. One advantage of a humanized antibody is that when it is administered to a human patient, the antigenic response is typically reduced compared to the response generated when a murine antibody is administered.

Some ligands that are provided are chimeric antibodies that consist of murine and human sequences. These chimeric antibodies differ from a fully humanized antibody in that they comprise the entire variable regions as listed in SEQ ID NOs: 1 and/or 2 in combination with the constant regions of both chains from a human immunoglobulin.

Other ligands are single chain antibodies that comprise an artificial linker sequence that bridges the $V_L$ and $V_H$ regions of an antibody, resulting in a single chain of amino acid residues containing both of the $V_L$ and $V_H$ regions. Thus, ligands of this type include: (1) single chain antibodies including miniantibodies (i.e., scFv fragments, which, for example, are linked to proline-rich sequences and oligomerization domains; see, e.g., Plückthun A. and Pack P., Immunotechnology, 1997, Vol. 3, pp. 83-105, the disclosure of which is incorporated herein by reference), and (2) single chain Fv (scFv), which incorporate the entire antibody binding region in one single polypeptide chain.

For instance, single chain antibodies can be formed by linking the V-genes to an oligonucleotide which has been constructed as a linker sequence that connects the C terminus of the first V region with the N-terminus of the second V region. So in one configuration, the arrangement can be represented as $V_H$-Linker-$V_L$. Another arrangement can be represented as: $V_L$-Linker-$V_H$. Thus, both, $V_H$ and $V_L$ can be present at the N-terminal domain (Huston J S et al., Int. Rev. Immunol., 1993, Vol. 10, pp. 195-217; Raag R. and Whitlow M., FASEB J., 1995, Vol. 9, pp. 73-80). The sequence that is used as linker sequence can, e.g., have a length of up to 150 Å, and more preferably up to 40 Å (measured in the stretched state).

Peptide linkers and their use are well-known in the art. See, e.g., Huston et al., Proc. Nat'l Acad. Sci. USA 8:5879 (1988); Bird et al., Science 242:4236 (1988); Glockshuber et al., Biochemistry 29:1362 (1990); U.S. Pat. Nos. 4,946,778, 5,132,405 and Stemmer et al., Biotechniques 14:256-265 (1993). In some instances, the peptide linker has no specific biological activity other than to join the regions or to preserve some minimum distance or other spatial relationship between the $V_H$ and $V_L$. However, the constituent amino acids of the peptide linker can be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Gly-Ser (SEQ ID NO:11), preferably 2, 3, 4, 5, or 6 such sequences. However, it is to be appreciated that some amino acid substitutions within the linker can be made. For example, a valine can be substituted for a glycine.

Linker sequences containing glycine and serine are useful because of their flexibility. Glutamine and lysine are useful because of their solubility in aqueous solution. The single chain antibodies can also be aggregates (e.g., as trimers, oligomers or multimers). In some antibodies, however, the linker sequence is omitted, in which case the $V_H$ and $V_L$ chains are directly connected. Bispecific antibodies are macromolecular, heterobifunctional cross-linkers having two different binding specifications within one single molecule [bispecific (bs) IgGs, bs IgM-IgAs, bs IgA-dimers, bs $(Fab')_2$, $bs(scFv)_2$, diabodies, and bs bis Fab Fc (see, e.g., Cao Y. and Suresh M. R., Bioconjugate Chem., 1998, Vol. 9, pp. 635-644, the disclosure of which is incorporated herein by reference) belong to this group].

The antibody ligands that are provided typically have an in vivo half live of at least 5 days, more preferably of at least 10 days, most preferably at least 20 days.

B. Determining Ligand Activity

As indicated above, the ligands that are disclosed herein have a factor VIIIa-cofactor activity or factor IXa-activating activity. As such, they promote the procoagulant activity of factor IXa. The function of the ligands does not require the presence of factor VIII or factor VIIIa. Accordingly, the function of the ligands is not negatively affected by the presence of inhibitors against factor VIII/factor VIIIa. Instead, these ligands can promote the procoagulant activity of factor IXa, even in the presence of such inhibitors.

Ligand activity, namely the ability to increase FIXa procoagulant activity, can be measured by the following FVIII assay:

Test reactions are performed in PPN tubes (Micronic, The Netherlands) in a 37° C. water bath as follows to test function of the ligands: 220 µl HNaBSA5-buffer (25 mM Hepes, 175 mM NaCl, 5 mg/ml BSA, pH 7.35) containing 13.6 µM phospholipids (vesicles; 60% 1-2-Dioleoly-sn-Glycero-3-Phosphocholine, 40% 1-Palmitoyl-2-Oleoyl-sn-Glycero-3-Phosphoserine) and 6.8 mM $Ca^{2+}$ is prewarmed to 37° C. 20 µl FX, 20 µl FIXa and 40 µl of the respective cofactor are added yielding a reaction mixture that contains 10 µM phospholipid and 5 mM $CaCl_2$. After 0.5, 1, 2, 4, 6, 8, 10, 15, 20, 25 and 30 minutes, 20 µl aliquots are taken from this reaction mix and transferred into 500 µl ice-cold EDTA-buffer (50 mM Tris pH 8.3, 9 mM EDTA, 428 mM NaCl) to stop FXa formation. The amount of FXa generated is determined by mixing 210 µl of the diluted aliquot with 40 µl of a substrate-αNAPAP mixture (5 mM Pefachrome FXa (Pefa-5523)+6 µM α NAPAP; Pentapharm) in a 96 well-microplate and measuring of the rate of chromogenic substrate cleavage (OD/[min]) at 405 nm at 37° C. in a microplate reader. The FXa concentration is calculated for each time point from a standard calibration curve made with known amounts of FXa. This experiment is performed with 11 nM FIXa (final concentration in the reaction mixture) and the optimal antibody concentration (normally 25 nM) in combination with several different FX (substrate) concentrations (0, 10, 20, 30, 40, 60, 80, 100, 125, 150, 200, 250 nM FX). The resultant FXa-formation rates are plotted as function of the FX concentration and the Michaelis-Menten constants ($V_{max}$ and $K_M$) calculated by fitting the curve to a hyperbola using the solver function of Windows Excel. $K_{cat}$ is calculated according to $V_{max}=k_{cat}$ [FIXa] and the catalytic efficiency according to cat.eff.=$k_{cat}/K_M$.

Figure 3:
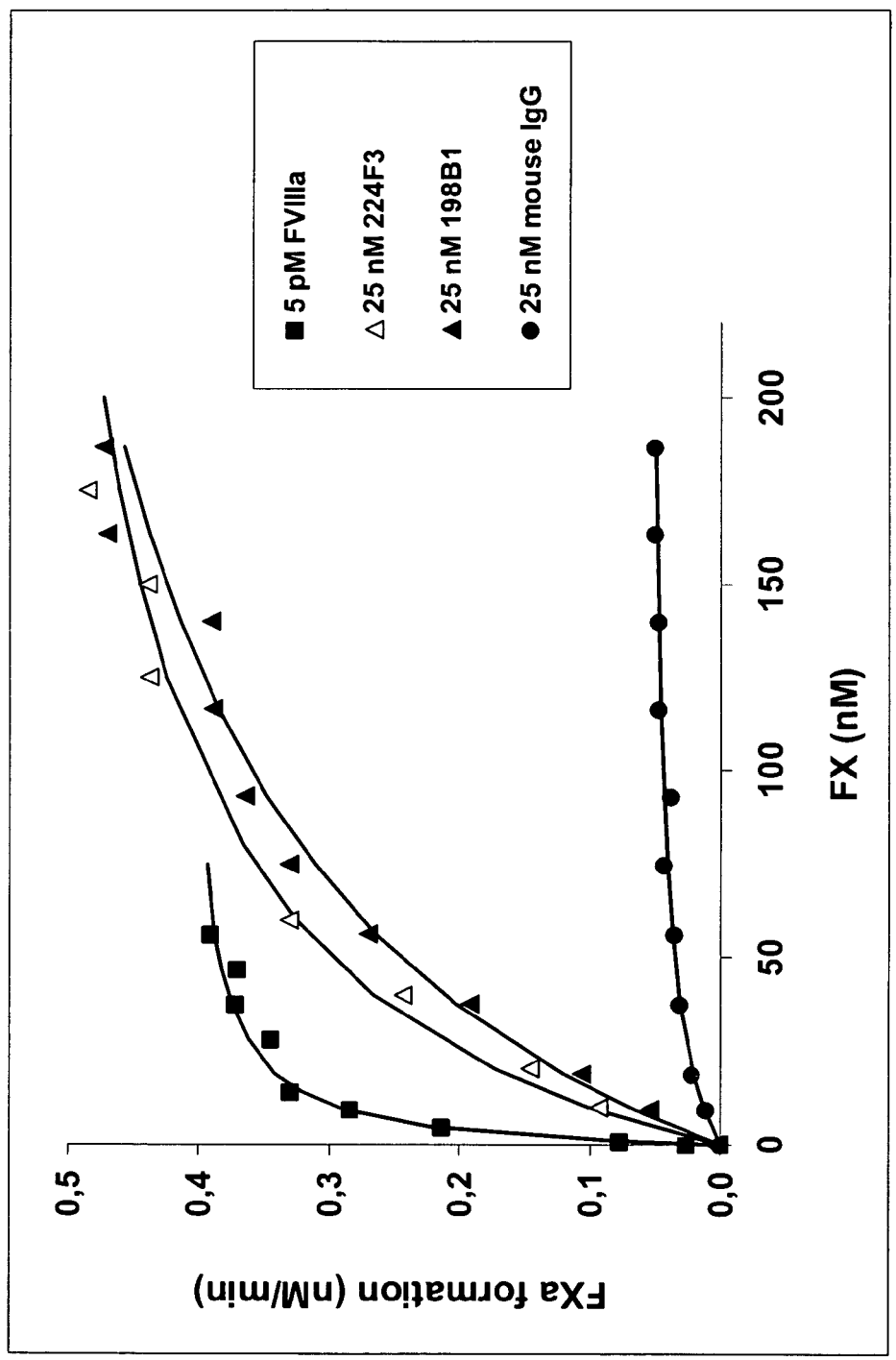
FIG. 3 shows a kinetic analysis of FIXa-catalyzed FX activation by an antibody-FIXa complex; a FVIIIa-FIXa complex; and FIXa without effector. Kinetic parameters are summarized in Table 1 below (Abscissa: FX [nM]; ordinate: FXa formation rate [nM/min]; filled circle: 25 nM mouse IgG; filled triangle: 25 nM antibody 198B1; open triangle: 25 nM antibody 224F3; filled square 5 pM FVIIIa).

The factor IXa ("FIXa") activating antibody 198B1 (disclosed in WO 01/19992) and the antibody 224F3 were characterized by determining the kinetic parameters of factor X ("FX") activation by the FIXa-antibody complexes. Rates of FX activation were measured at different substrate (i.e. human FX concentrations) in a reaction mixture that contained 11 nM FIXa, 25 nM of the respective antibody and FX concentrations between 0 nM and 150 nM. The rate of FX activation (nM/min) was plotted as function of the FX concentration and the Michaelis-Menten constants ($K_m$ and $V_{max}$) were obtained by fitting the curve to a hyperbola using the solver function of Windows Excel (FIG. 3). The turn-over-number, $k_{cat}$, was calculated by dividing $V_{max}$ by the enzyme-complex concentration. Antibodies 198B1 and 224F3 increased the $k_{cat}$ of FX activation by FIXa approximately tenfold, (see Table 1 and subsequent text). FIXa without cofactor, as well as FIXa in presence of 25 nM non-specific polyclonal mouse IgG, gave identical hyperbolas and allowed calculation of the kinetic parameters of FIXa without effector. For comparison, Michaelis-Menten hyperbolas were also determined at different factor VIIIa ("FVIIIa") concentrations. The $V_{max}$ obtained with antibody 198B1 and 224F3 was similar to that determined in the presence of 5 pM factor VIII ("FVIII"), an amount of FVIII that corresponds to a FVIII activity of 16 mU/ml or 1.6% of the plasma concentration. Furthermore, FVIII decreased the $K_m$ of FIXa approximately 2.5-fold (independent from the actual FVIIIa concentration). Ab 224 F3 did not significantly influence the $K_m$ of FX for FIXa, but 198B1 caused a 2-fold increase in $K_m$. However, in all cases, the $K_m$ was far below the concentration of FX in human plasma (136 nM). Further, only $K_{cat}$, but not the $K_m$ was affected by the antibody concentration. Finally, antibody 224F3 which contained all the sequences listed in SEQ ID NOs. 1 and 2, and thus also SEQ ID NOs. 3 to 8, showed the highest catalytic efficiency ($k_{cat}/K_M$), making it the most efficient antibody (see Table 1, herein below). The catalytic efficiency in terms of the Michaelis-Menten kinetics ($k_{cat}/K_M$) is increased by 688% in comparison with FIXa without effector.

Kinetic parameters of FX activation by FIXa without effector and FIXa-antibody complexes:

TABLE 1

|  | Vmax (nM/min) | $K_M$ (nM) | $k_{cat}$ (min$^{-1}$) | $k_{cat}/K_M$ (min$^{-1}$ nM$^{-1}$) |
|---|---|---|---|---|
| FIXa without effector: | 0.063 | 34.2 | 0.0057 | 0.16 × 10$^{-3}$ |
| FIXa-198B1 complex (11 nM FIXa, 25 nM IgG) (cf. 198/B1, 198/AB2 in WO 01/19992 A2) | 0.66 | 84.3 | 0.060 | 0.71 × 10$^{-3}$ |
| FIXa-224F3 complex (11 nM FIXa, 25 nM IgG) | 0.59 | 48.0 | 0.053 | 1.10 × 10$^{-3}$ |

Figure 4:
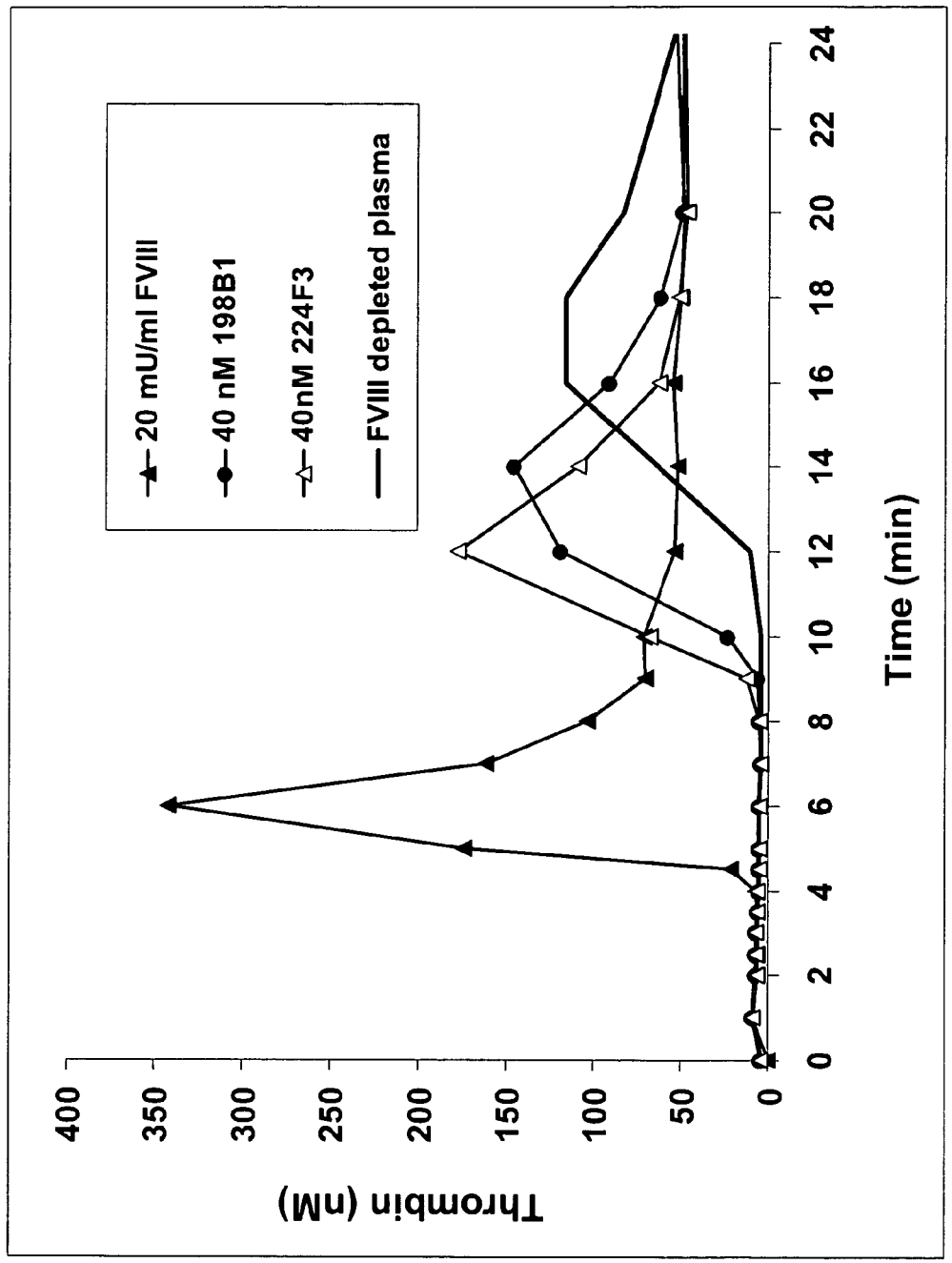
FIG. 4 shows time courses of thrombin-generation in FVIII-depleted plasma. Graphs show thrombin generation in FVIII-depleted plasma with and without antibodies (solid line: FVIII depleted plasma; filled circle: 40 nM antibody 198B1; open triangle: 40 nM antibody 224F3; filled triangle: 20 mU/ml FVIII. Abscissa: t [min], ordinate: thrombin [nM]).

To demonstrate that the ligands provided herein (e.g., antibody and antibody derivatives) also exhibit FVIII-like activity in human plasma, thrombin generation experiments were conducted in FVIII-deficient plasma. This assay system involved the whole intrinsic coagulation cascade, from FXIIa to formation of thrombin, as well as the inactivation of the coagulation factors by the plasma protease inhibitors antithrombin and $a_2$-macroglobulin. A time course of thrombin generation was characterized by a lag-phase which reflects the initiation of coagulation, that is followed by a burst of thrombin formation. Thrombin as well as other serine proteases, were subsequently inhibited by antithrombin and $a_2$-macroglobulin. First, the effect of FIXa-activating antibodies on thrombin generation in FVIII-deficient plasma obtained after immunodepletion of normal plasma with an antibody against FVIII was examined. For comparison, experiments were performed with FVIII (FIG. 4). The addition of FVIII had two effects on thrombin generation in FVIII-depleted plasma: (i) the thrombin-burst occurred earlier, which is indicative of a shortening of the clotting time, and (ii) the amount of thrombin that was generated, increased. Antibodies 198B1 and 224F3 show the same general effects (FIG. 4), although to a different extent. Here, too, antibody 224F3 (open triangle) proved to be more efficient than the other antibody. As in model systems, the effect of the antibodies on thrombin generation was found to be dependent on antibody concentration. For both antibodies, the optimal effect on thrombin generation was at 40-60 pmol antibody/ml plasma, which is equal to the FIX concentration (40 pmol/ml) determined in depleted plasma with a quantitative ELISA.

Figure 5:
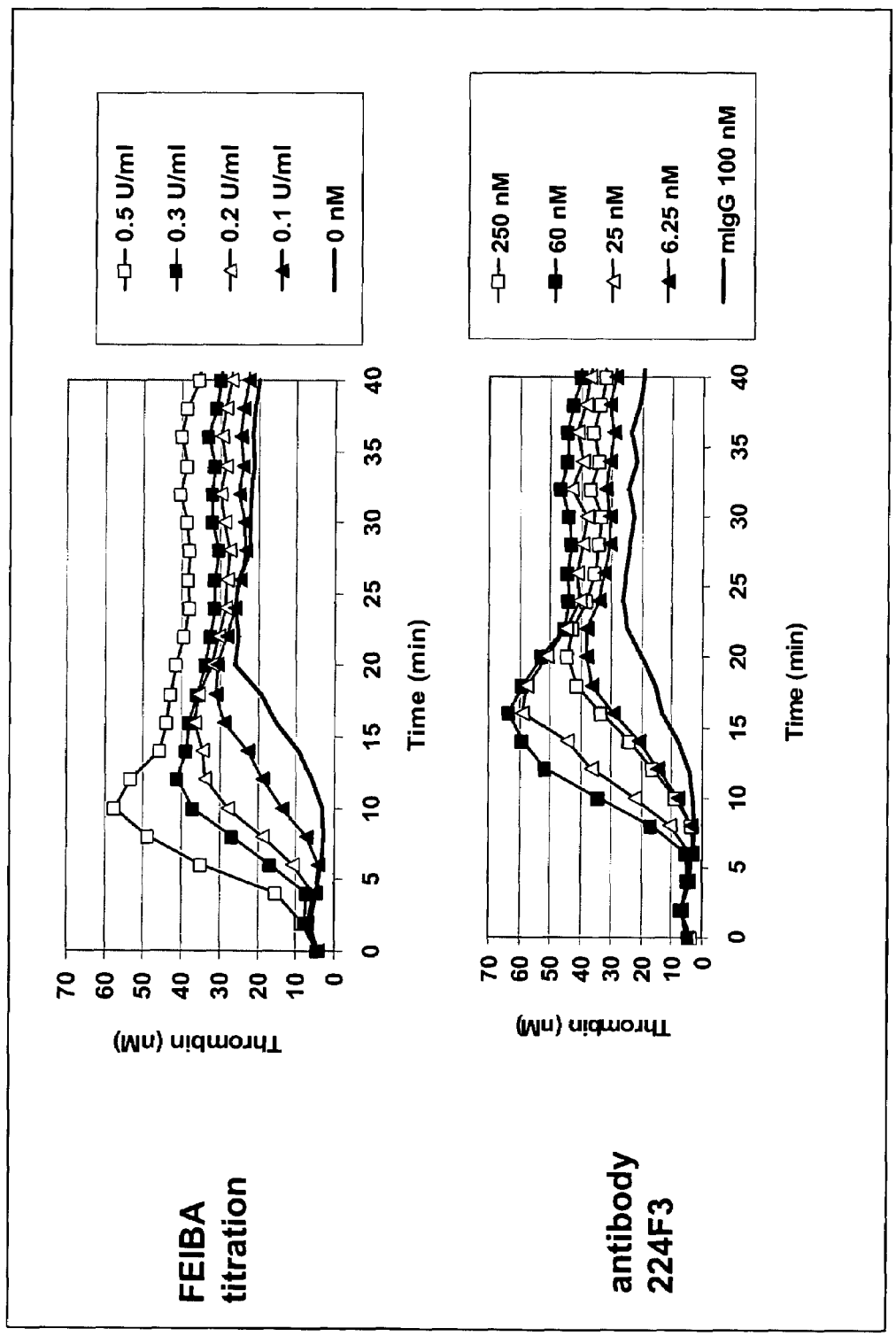
FIG. 5 shows time courses of thrombin generation in FVIII inhibitor plasma. Graphs show thrombin generation in FVIII inhibitor plasma with different concentrations of FEIBATm or procoagulant antibody 224F3. As negative controls, thrombin generations in FVIII inhibitor plasma with unspecific mouse IgG and without supplementation are shown. Upper graph: abscissa: t [min]; ordinate: thrombin [nM]; open square: 0.5 U/ml FEIBA™; filled square: 0.3 U/ml FEIBA™; open triangle: 0.2 U/ml FEIBA™; filled triangle: 0.1 U/ml FEIBA™; solid line: 0 nM FEIBA™. Lower graph: abscissa: t [min]; ordinate: thrombin [nM]; open square: 250 nM antibody 224F3; filled square: 60 nM antibody 224F3; open triangle: 25 nM antibody 224F3; filled triangle: 6.25 nM antibody 224F3; solid line: 100 nM unspecific mouse IgG.

Immunodepleted FVIII-deficient plasma contains residual FVIII activity. In contrast, FVIII inhibitor plasma with a titer >10 BU, contains not only FVIII neutralizing antibodies, but also lacks FVIII activity. To investigate whether the activity of the procoagulant antibodies is affected by the presence of FVIII inhibitors, thrombin generation experiments were repeated in FVIII inhibitor plasma. Due to the presence of inhibitors, it was not possible to compare the activity of the procoagulant antibodies with FVIII. Thus, the procoagulant activity of the antibodies was compared with FEIBA™ (Baxter Healthcare Corp. or Baxter AG), an activated prothrombin complex therapeutic, frequently used to treat bleeding episodes in inhibitor patients. In plasma from inhibitor patients, increasing amounts of FEIBA™ have the same effect on thrombin generation as FVIII has in FVIII-depleted plasma (FIG. 5). When the procoagulant antibodies were applied as FIXa stimulating agents, their effects were even more pronounced in inhibitor plasma than in FVIII-depleted plasma. FIG. 5 shows the time course of thrombin generation obtained in the presence of antibody 224F3. At optimal conditions, thrombin formation occurred 10 mins earlier than in the absence of antibody. Again, antibody concentrations equimolar to the FIX concentration in plasma show the highest thrombin formation potential.

C. Ligand Production

Antibody ligands can be prepared by methods known from the art, e.g., by conventional hybridoma techniques, or by means of phage display gene libraries, immunoglobulin chain shuffling or humanizing techniques (see, e.g., Harlow E. and Lane D., in: Antibodies, A Laboratory Manual, Cold Spring Harbor Laboratory, 1988).

For example, polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent can include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal antibodies can be prepared using conventional hybridoma methods, (see, e.g., Kohler & Milstein, *Nature* 256:495 (1975); and Antibodies, A Laboratory Manual, Cold Spring Harbor Laboratory, 1988, Eds. Harlow and Lane, pp. 148-242). In a hybridoma method, a mouse, hamster, or other appropriate host animal, is typically immunized with an immunizing agent to elicit lymphocytes that produce or are capable of producing antibodies that will specifically bind to the immunizing agent. Immunization can, for example, be effected with factor IX, factor IXaα or completely activated factor IXaβ, or with fragments thereof. The hybridomas are selected with a view to the fact that the ligands in the supernatants of the hybridoma cells bind to factor IX/factor IXa and cause an increase of the procoagulant activity of factor IXa. The increase in the procoagulant activity can, for example, be proven by assay methods known in the art for the measurement of factor VIII-like activity, e.g., chromogenic assays (see, e.g., Example 2 below). Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, pp. 59-103 (1986)).

Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Alternatively, the proteinaceous ligands of that are disclosed can also be produced by recombinant production methods. In this embodiment, the DNA sequence of the ligands can be determined by known techniques, and the entire antibody DNA or parts thereof can be expressed in suitable systems. Recombinant production methods can be used, such as those involving phage display, synthetic and natural libraries, expression of the antibody proteins in known expression systems, or expression in transgenic animals (Jones et al., Nature, 1986, Vol. 321, pp. 522-525; Phage Display of Peptides and Proteins, A Laboratory Manual, 1996, Eds. Kay et al., pp. 127-139; U.S. Pat. No. 4,873,316; Vaughan T. J. et al., Nature Biotechnology, 1998, pp. 535-539; Persic L. et al., Gene, 1997, pp. 9-18; Ames R. S. et al., J. Immunol. Methods, 1995, pp. 177-186).

Recombinantly produced antibodies as ligands can be produced by means of conventional expression vectors, such as bacterial vectors (e.g., pBr322 and its derivatives), pSKF or eukaryotic vectors (e.g., such as pMSG and SV40 vectors). Those sequences that encode the antibody can be provided with regulatory sequences that regulate the replication, expression and/or secretion from the host cell. These regulatory sequences comprise, for instance, promoters (e.g., CMV or SV40) and signal sequences. The expression vectors can also comprise selection and amplification markers, such as the dihydrofolate reductase gene (DHFR), hygromycin-B-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, fibroblasts, insect cells, yeast or bacteria such as *E. coli*. In some instances, cells are used that allow for optimal glycosylation of the expressed protein.

Fab fragments or F(ab)$_2$ fragments as ligands can be produced according to methods known from the prior art, e.g. by cleaving an antibody with proteolytic enzymes, such as papain and/or pepsin, or by recombinant methods. Fab and F(ab)$_2$ fragments can also be prepared by phage display gene library methods (Winter et al., 1994, Ann. Rev. Immunol., 12:433-455).

Methods of making scFv antibodies have been described. See, Huse et al., supra; Ward et al. supra; and Vaughan et al., supra. In brief, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell. The scFv that specifically bind to the desired antigen are typically found by panning of a phage display library. Panning can be performed by any of several methods. Panning can conveniently be performed using cells expressing the desired antigen on their surface or using a solid surface coated with the desired antigen. Conveniently, the surface can be a magnetic bead. The unbound phage are washed off the solid surface and the bound phage are eluted.

Human antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368: 856-859 (1994); Morrison, *Nature* 368:812-13 (1994); Fishwild et al., Nature Biotechnology 14:845-51 (1996); Neuberger, *Nature Biotechnology* 14:826 (1996); Lonberg & Huszar, *Intern. Rev. Immunol.* 13:65-93 (1995).

Other protein ligands can be prepared using methods known in the art, e.g., by molecular modeling (see, e.g., Grassy G. et al., Nature Biotechnol., 1998, Vol. 16, pp. 748-752; Greer J. et al., J. Med. Chem., Vol. 37, pp. 1035-1054; or Rees A. et al., in: "Protein Structure Prediction: A practical approach", (Sternberg M. J. E., ed.) IRL press, 1996, chap. 7-10, pp. 141-261).

Ligands can be purified by various methods described in the art, e.g., by ammonium sulfate precipitation, affinity purification (e.g., protein G-Sepharose), ion exchange chromatography, or gel chromatography. A number of methods can be used to show that the ligands disclosed herein bind to factor IX/factor IXa, and/or increase the procoagulant activity of factor IXa, and/or have factor VIII-like activity, including, for instance: the one step coagulation test (see, e.g., Mikaelsson and Oswaldson, Scand. J. Haematol., Suppl., 33, pp. 79-86, 1984), or chromogenic tests, such as COATEST VIII: C® (Chromogenix) or Immunochrom (IM-MUNO). In principle, all the methods used for determining factor VIII activity can be used. As the control blank value for the measurements, unspecific mouse-IgG antibody, for example, can be used.

III. Nucleic Acids and Transformed Cells

Also provided are nucleic acids (e.g., a DNA or a RNA) that encode the ligands that are disclosed herein. Certain nucleic acids, for example, include one or both of the DNA sequences disclosed in FIGS. 6 and 7.

Host cells that contain such nucleic acids and express a ligand as disclosed herein are also provided. Such cells are preferably immortalized. Usually these cells form a uniform cell line. The cell can also be a hybridoma cell.

Methods of producing a ligand such as an antibody or antibody derivative using a cell and/or a nucleic acid as described above are also provided. These methods generally involve inserting a nucleic acid encoding a ligand into an expression vector to form an expression construct. The resulting construct is then introduced into a host cell using conventional methods to express the protein ligand. The protein ligand is then separated from at least one other component of the host cell. Typically, the protein is purified so that the ligand is biologically pure as defined above.

IV. Exemplary Utilities

A. Treatment Methods/Pharmaceutical Compositions

The ligands that are provided are suitable for therapeutic use in the treatment of coagulation disorders, e.g., in the treatment of hemophilia A and factor VIII inhibitor patients. Ligands can be administered by any method suitable to effectively administer the therapeutic agent to the patient, e.g. by oral, subcutaneous, intramuscular, intravenous or intranasal administration.

A "patient" typically is a human patient but can include other mammals. Thus the methods are applicable to both human therapy and veterinary applications. In the preferred embodiment the patient is a mammal, preferably a primate, and in the most preferred embodiment the patient is human.

Therapeutic agents can be produced as compositions that comprise a pharmaceutically effective amount of the above defined ligands as the active agent in a pharmaceutically acceptable carrier and/or diluent. Therefore, pharmaceutical compositions comprising a ligand as defined above and a pharmaceutically acceptable carrier and/or diluent are also provided. Such pharmaceutical compositions can be present either in liquid or in powderized form. Moreover, the pharmaceutical compositions can comprise mixtures of different ligands or derivatives thereof. Factor IX and/or factor IXa. Factor IXa can be present as factor IXaα and/or factor IXaβ and/or factor IXα. An example of a liquid for a carrier or diluent is saline. The solutions are sterile, sterilization being effected by conventional methods.

The present invention also comprises the use of a ligand as defined above for the manufacture of a medicament for the treatment of patients afflicted with blood coagulation disorders.

The ligands that are described herein can be utilized in a variety of ways to develop drugs against haemophilia A. One approach involves reducing an antibody to a format that lacks the Fc region (e.g., to a Fab or F(ab')2 form) and to humanize the antibodies. Either chimeric or fully humanized antibody fragments can be used to enter the clinical trial. Another option is to design a small molecule from an antibody binding site. The effector function of the antibody is achieved by binding of the antibody that induces conformational changes in FIXa. Such effects can also be achieved by a small proteomimetic or peptidomimetic that corresponds to the antibody paratope. Because an antibody is essentially a biological molecule that presents a combinatorial array of peptide elements in three-dimensional space, compounds with FVIII-like activity (i.e., an FIXa activator) can be developed that can be orally administered and that is also active in presence of FVIII inhibitors. Compounds of this type are can be used advantageously in haemophilia A treatment, since they avoid many drawbacks associated with current treatments, such as intravenous injection, a troublesome route especially for small children.

The ligands or pharmaceutical compositions can be present in lyophilized form for storage and then subsequently suspended in a suitable solvent before administration to a patient. This method has proven generally advantageous for conventional immunoglobulins, and known lyophilization and reconstitution methods can be applied in this case.

Some of the compositions that are provided are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Certain compositions include ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions can also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that protein ligands (e.g., antibodies) when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration can include a ligand (e.g., antibody) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., *Remington's Pharmaceutical Science* (15th ed., 1980) and Goodman & Gillman, *The Pharmacologial Basis of Therapeutics* (Hardman et al., eds., 1996)).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions containing the provided ligands can be administered for therapeutic or prophylactic treatments. In therapeutic applications, compositions are administered to a patient suffering from a blood coagulation disease in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of a blood disorder in a patient is referred to as a "prophylactically effective dose." The particular dose required for a prophylactic treatment will depend upon the medical condition and history of the patient, as well as other factors such as age, weight, gender, administration route, efficiency, etc.

An appropriate dose can be determined by one skilled in the art using known techniques (see, e.g., Ansel et al., *Pharmaceutical Dosage Forms and Drug Delivery*; Lieberman, Pharmaceutical Dosage Forms (vols. 1-3, 1992), Dekker, ISBN 0824770846, 082476918X, 0824712692, 0824716981; Lloyd, *The Art, Science and Technology of Pharmaceutical Compounding* (1999); and Pickar, Dosage Calculations (1999)).

Certain methods generally comprise administering a pharmaceutically effective amount of one or more of the ligands as defined above to a patient. The pharmaceutically effective amount of the ligand typically ranges from 0.005 to 50 mg per kg bodyweight. The blood coagulation disorders that can be treated include, but are not limited to, hemophilia A and hemorrhagia diathesis. The group of patients to be treated can include or be confined to hemophilia inhibitor patients.

B. Non-Therapeutic Utilities

In addition to the foregoing applications, the ligands can be used for industrial applications, e.g., for the purification of factor IX/factor IXa by means of affinity chromatography, or as a component of detection methods (e.g. ELISA assays), or as an agent for identification of an interaction with functional domains of a target protein.

If the ligands are used in identification methods, the ligands are typically joined to a label. A variety of methods are known for conjugating a protein ligand (e.g., an antibody) to a label (see, e.g., Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982)). The lifetime of radiolabeled peptides or radiolabeled antibody compositions can be extended by the addition of substances that stabilize the radiolabeled peptide or antibody and protect it from degradation. Any substance or combination of substances that stabilize the radiolabeled peptide or antibody can be used including those substances disclosed in U.S. Pat. No. 5,961,955.

The following examples are provided to illustrate certain aspects of the ligands, compositions and methods that are provided. These examples, however, should not be construed to limit the scope of the claimed invention.

EXAMPLE 1

Generation of Hybridoma Cell Lines

Balb/c mice were immunized four times with human FIXa at one week intervals. 100 µg antigen per immunization was injected using $Al(OH)_3$ as adjuvant. Spleen cells were obtained three days after the last immunization and hybridoma cell lines were established according to standard procedures (Köhler and Milstein, Nature 256:495 (1975)). Per mouse, 880 hybridoma cell lines were grown in 96-well plates, first in HAT selection medium and later in normal growth medium (RPMI-1640). After four to five weeks, supernatants were screened for FVIII-like activity in a screening assay (see below). Cell lines expressing antibodies identified as displaying FVIII-like activity were subcloned four to six times to ensure that the cell line was monoclonal and stable.

Isolation of FIXa Specific Antibodies Exhibiting FVIII-like Activity.

A series of antibodies specific for human FIXa was isolated that exhibited FVIIIa-like activity using the following screening procedure: Balb/c mice were immunized with FIXa and, after immortalization of spleen cells, hybridoma cell lines were obtained.

EXAMPLE 2

Screening Assay

The commercially available test-kit for FVIII activity, the COATEST VIII:C/4® (Chromogenix) was used to screen hybridoma supernatants for antibodies that displayed FVIII-like activity. The assay was performed essentially as described by the manufacturer, except that the sample and reagent volumes were reduced to a 96-well format and reactions were not stopped after 5 min, but were allowed to proceed for three hours. Furthermore, 20 ng human FIXa was added in each well to increase the sensitivity of the assay. The COATEST VIII:C/4® was an all-in-one assay and cleavage of FX to FXa by FIXa, as well as cleavage of the FXa-specific chromogenic substrate Bz-Ile-Glu-Gly-Arg-pNA (S-2222), took place in the same reaction well. Stimulation of catalytic activity of FIXa by a specific antibody that functioned as a cofactor of FIXa resulted in FXa generation and thus in cleavage of the chromogenic substrate. Released p-nitroaniline was measured at 405 nm in a 96-well microplate reader (iEMS-Reader, Labsystems, Finland).

Individual supernatants from hybridoma cells were screened for FVIII-like activity. Briefly, a mixture of the enzyme FIXa, the substrate FX, phospholipids and $Ca^{2+}$ were incubated with hybridoma supernatants. Agonistic antibodies, i.e. FIXa binding antibodies that were able to augment FIXa protease activity, accelerated FIXa-mediated FXa formation. Generation of FXa, indicative for the presence of agonistic antibodies, was monitored with a FXa specific substrate and liberation of p-nitroaniline monitored. Supernatants of hybridoma cell lines expressing non-specific mouse IgG were used as negative controls. In parallel, hybridoma supernatants were tested for FIXa binding antibodies by ELISA. This screening procedure allowed for the discovery of 88 antibodies exhibiting different degrees of FIXa-agonistic activity out of 5280 hybridoma supernatants tested in total, whereas approximately 60% of the hybridoma cell lines produced FIXa binding antibodies.

EXAMPLE 3

Production and Purification of Procoagulant Antibodies

Monoclonal hybridoma cell lines were grown in a standard growth medium (e.g., RPMI-1640) for two to three weeks. IgG were purified over Protein G-Sepharose 4 Fast Flow (Amersham Biosciences) according to standard procedures (see, e.g., Jungbauer, A. et al., (1989) J. Chromatogr. 476:257-268).

EXAMPLE 4

Function of Procoagulant Antibodies.

All monoclonal antibodies displaying FVIII-like activity were purified and further characterized by FXa-generation assays. Two monoclonal antibodies, termed 198B1 and 224F3, were identified to show the most pronounced FVIII activity. The in depth characterization of these two antibodies was further described. Antibody 198B1 was found to be strictly specific for human FIX and FIXa, since ELISA and Western blot analysis did not show any binding to bovine or murine FIX. Furthermore, incubation with bovine FIXa did not result in FXa generation. However, antibody 224F3 bound to human and bovine FIX and FIXa, but not to murine. Competition ELISAs revealed, that the two antibodies interacted with the same binding site on FIX. On the other hand, the antibodies did not compete with FVIIa for binding to FIXa.

Detection of Factor Xa Formation Inducing Activity of Certain Antibodies

Proteolytic conversion of FX into its enzymatically active form, FXa, was achieved by contacting FX with the intrinsic factor X-activating complex. This complex consisted of the protease FIXa bound to its cofactor FVIIIa on a negatively charged phospholipid surface in the presence of $Ca^{2+}$ ions (van Dieijen, G., et al. (1985) Thromb. Haemost. 53:396-400; and Rosing, et al. (1985) Blood 65:319-332). To quantitatively determine the ability of the procoagulant antibodies to convert FX to FXa, assays were performed as follows:

Reactions were performed in PPN tubes (Micronic, The Netherlands) in a 37° C. water bath as follows: 220 μl HNaBSA5-buffer (25 mM Hepes, 175 mM NaCl, 5 mg/ml BSA, pH 7.35) containing 12.8 μM phospholipids and 5.9 mM $Ca^{2+}$ were prewarmed to 37° C. 20 μl FX, 20 μl FIXa and 40 μl of the respective cofactor (antibody or as control thrombin-activated rFVIII) were added yielding a reaction mixture that contained 10 μM phospholipid, 5 mM $CaCl_2$ and 0.5 mg/ml BSA. The final concentrations of FIXa, rFVIII, FX and antibody were dependent on the kind of analysis. After varying time intervals, aliquots (20 μl) taken from this reaction mix were transferred into 500 μl ice-cold EDTA-buffer (50 mM Tris pH 8.3, 9 mM EDTA, 428 mM NaCl) to stop FXa formation. The amount of FXa generated was determined by mixing 210 μl of the diluted aliquot with 40 μl of a substrate-αNAPAP mixture (5 mM Pefachrome FXa (Pefa-5523)+6 μM αNAPAP; Pentapharm) in a 96 well-micro plate and the rate of chromogenic substrate cleavage (ΔOD/min) measured at 405 nm at 37° C. in a microplate reader. The FXa concentration was calculated for each time point from a standard calibration curve made with known amounts of FXa.

Figure 2A:
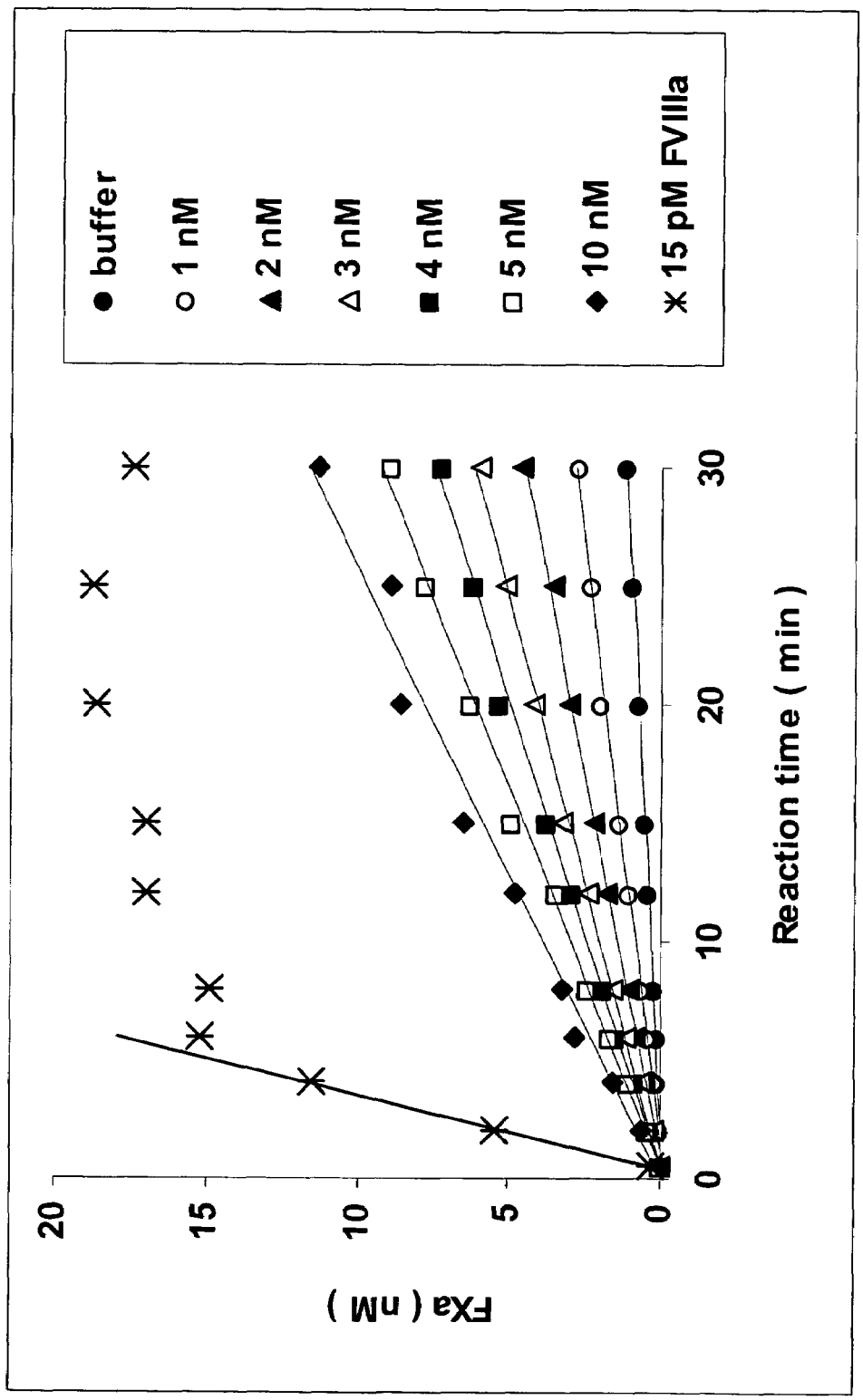
FIG. 2A is a time course of FXa generation at varying antibody concentrations (abscissa: t [min]; ordinate: FXa [nM]; cross: 15 pM FVIIIa; filled diamond: 10 nM 224F3; open square: 5 nM; filled square: 4 nM; open triangle: 3 nM; filled triangle: 2 nM; open circle: 1 nM; filled circle: buffer).
Figure 2B:
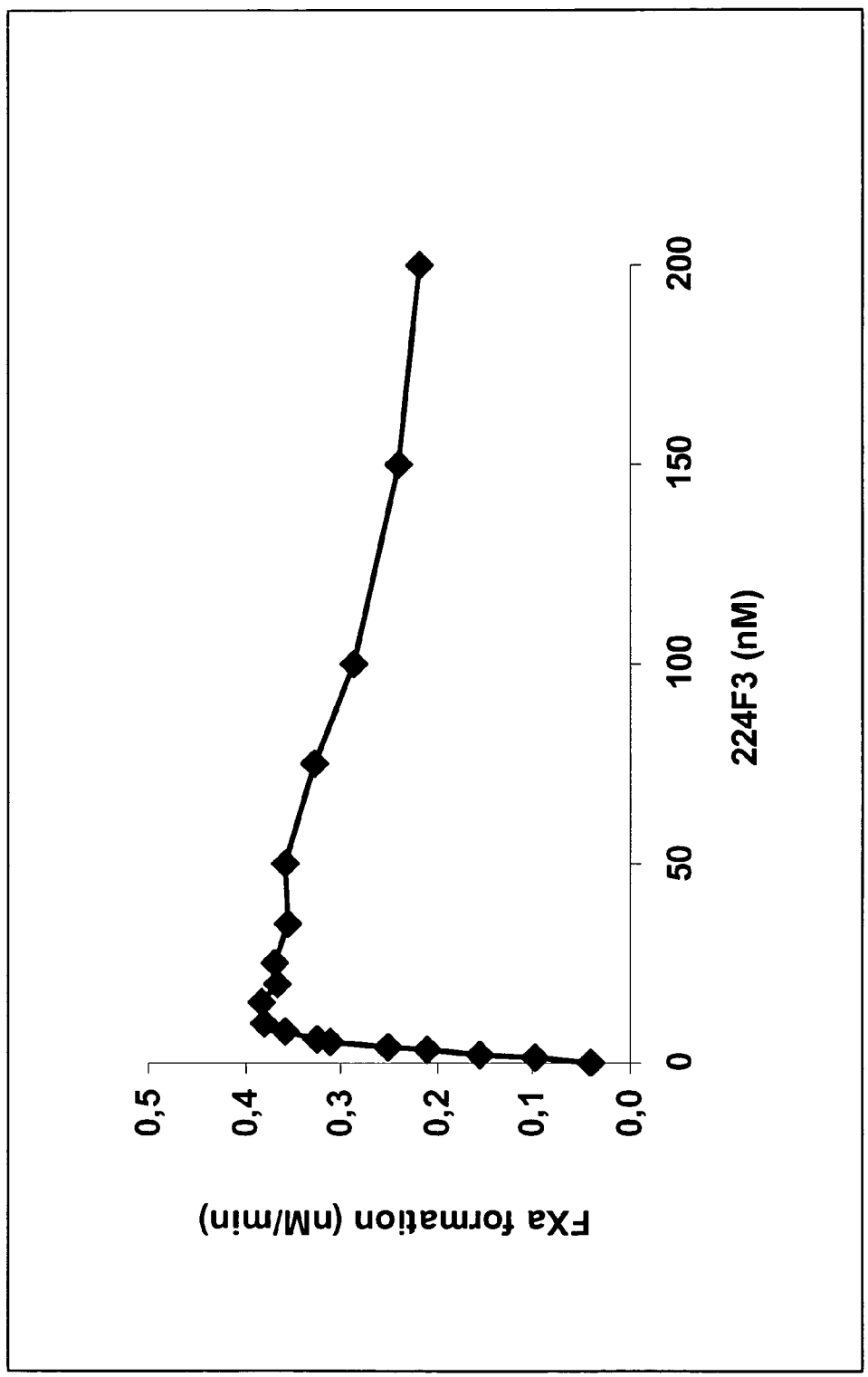
FIG. 2B is an antibody titration curve (abscissa: 224F3 [nM]; ordinate: FXa formation rate [nM/min]).

In a first set of experiments, 11 nM FIXa, 150 nM FX and 10 uM phospholipid vesicles were incubated with varying amounts of antibody (5-200 nM) in a reaction mixture containing 5 mM $Ca^{2+}$ ions and FXa generation was followed with a FXa-specific chromogenic substrate. 224F3 gave more pronounced results than antibody 198B1. FXa-generation curves obtained with antibody 224F3 were shown in FIG. 2a. The antibody-mediated enhancement of the rate of FXa formation (nM FXa/min) was concentration dependent and, compared to the buffer control, a 10-fold rate enhancement was observed at the optimal antibody concentration. As negative control, buffer or non-specific polyclonal mouse antibodies were applied and both negative controls yielded identical background activation. For comparison, FXa generation assays were performed in presence of 17.5 pM of the natural cofactor FVIIIa. The curve obtained with FVIIIa was linear for approximately five minutes; thereafter, FXa generation stopped, presumably because of inactivation of FVIIIa through dissociation of its A2 domain. FXa generation with antibodies was linear for at least 30 min. Antibody titrations further revealed a dose-dependent effect on the rate of FXa formation (FIG. 2b). At 11 nM FIXa, a linear dose response was obtained up to a mAb concentration of approximately 5 nM (i.e., up to the presence of one binding site per FIXa molecule). Between antibody concentrations of 10 nM and 30 nM, the rate of FX activation reached a maximum and descended at higher antibody concentrations (FIG. 2b). In the case of 50 nM FIXa, linearity up to 25 nM antibody was obtained (data not shown). Thus, a linear dose response could be seen until FIXa was saturated with antibody.

No detectable amounts of FXa were formed when FIXa, FX, phospholipids or $Ca^{2+}$ ions were omitted from the reaction mixture. To rule out the possibility that the substrate FX was cleaved by traces of FXa via autocatalytic activation, FXa-generation assays were performed in the presence of 60 μM Pefablock Xa™ (Pentapharm). Pefablock was a competitive FXa inhibitor that completely inhibited FXa activity at this concentration. After subsampling into EDTA-buffer, Pefablock was diluted to 2 μM, a concentration that allowed FXa quantification. The same FXa generation rates were obtained in the absence and presence of Pefablock Xa™. These results indicated that FXa formation occurred when FXa that was present or generated in the reaction mixture was inhibited and excluded the possibility that autocatalysis contributed to antibody-mediated FXa generation. To summarize, the experiments described in this paragraph showed that the antibodies did not catalyze or induce a bypass reaction, but instead functioned as a specific cofactor for proteolytic activation of FX by FIXa.

EXAMPLE 5

SPR-measurements

Interaction of FIXa with the antibodies was investigated by Surface Plasmon resonance (SPR) technology using a BIACORE 300 Instrument (Biacore AG, Uppsala, Sweden). Polyclonal anti-mouse Fc antibodies were immobilized on a CM5 sensor chip and saturated with the respective monoclonal antibody. As a reference, a non-specific mouse IgG was used. Different concentrations of FIXa were applied to the chip and flowed through and the affinity constants were calculated from steady state analysis using the built in BIACORE program. The dissociation rate constants (Kd), calculated from the steady state binding were in good agreement with the kinetic curves, i.e. $4.77 \times 10^{-10}$ M for 224F3 and $3.55 \times 10^{-09}$ M for 198B1. Antibody 224F3 had the highest affinity for FIXa and, in all cases, binding was stronger in the presence of 5 mM $CaCl_2$.

FIG. 1 showed the binding of 5.56 nM FIXa to the two different monoclonal antibodies captured by anti-mouse Fcγ (RAMFc) in the presence of 5 mM $CaCl_2$. FIXa showed a lower affinity to the antibodies in the presence of 3 mM EDTA and did not bind to the unspecific mouse IgG.

EXAMPLE 6

Thrombin Generation

FVIII-depleted plasma or FVIII inhibitor plasma was defibrinated with 1 U/ml ancrod, with fibrin removed with a plastic stirring rod. 200 µl defibrinated plasma and 10 µl prediluted antibody were mixed in micronic tubes (see FIGS. 4 and 5). As control, rFVIII was used in place of FVIII-depleted plasma and FEIBA® in place of inhibitor plasma. The concentrations of mAb, rFVIII and FEIBA® were described in the "Brief Description of the Drawings" section. The mixture was prewarmed to 37° C. for 5 minutes and a 10 µl aliquot was transferred to 740 µl ice-cold cuvetbuffer (50 mM Tris, 175 mM NaCl, 0.5 mg/ml ovalbumin, 20 mM EDTA, pH 7.9) to determine the zero point. Afterwards 87.5 µl Pathromtin SL(Dade Behring; prewarmed to 37° C.) and 25 µl HNBSA5 containing 162.5 mM $CaCl_2$ (prewarmed to 37° C.) were added to initiate thrombin formation via the intrinsic coagulation pathway. After different time intervals, aliquots (10 µl) from the reaction mixture were transferred to 740 µl ice-cold cuvetbuffer to stop the thrombin formation. The amount of thrombin present in the diluted aliquots was determined in a microplate reader with the thrombin-specific chromogenic substrate S2238 (Chromogenix). The thrombin concentration was calculated for each time point from a standard calibration curve made with known amounts of thrombin.

The reagents of the experiments described in the description were the following. Human coagulation factors FIX, FIXa, FX, FXa and α-thrombin were purchased from Enzyme Research Laboratories (USA). Recombinant human coagulation factor VIII (rFVIII) was prepared by Baxter BioSciences (USA) (RECOMBINATE™). BSA was purchased from Calbiochem (USA). Human FVIII-depleted plasma was prepared by Baxter BioSciences (Austria) via immunodepletion and human FVIII-inhibitor plasma was prepared from patient plasma by Technoclon (Austria). Non-specific polyclonal mouse IgG was purchased from Sigma (USA). Phospholipid vesicles (DOPC:POPS 60:40) were prepared by Baxter BioSciences (Austria) from synthetic phospholipids (Avanti Polar Lipids, Inc., USA). Pathromtin SL was purchased from Dade Behring (USA) and Ancrod from NIBSC (UK). FEIBA® and DAPPTIN were obtained from Baxter BioSciences (Austria).

The interaction between FVIIIa and the serine protease FIXa was a prominent example of an effector function. Binding of the cofactor FVIIIa to FIXa converted the enzyme from a low activity form into a highly active protease by, among other things, inducing a conformational change in FXIa that led to enhanced FX-cleaving activity. In order to screen specific antibodies that induced a similar conformational change in the protease FIXa, a commercially available photometric factor VIII assay was adapted, which was widely used to measure FVIII activity in plasma. Although 60% of the cell lines screened expressed a FIX binding antibody, only 1.6% of the hybridoma supernatants showed FVIII-like activity in our screening assay. This was in line with our assumption, that activation of FIXa was a rare finding. Kinetic experiments showed that the antibodies enhanced the catalytic activity ($k_{cat}$) of FIXa approximately 10-fold, while the Km of FX for FIXa was hardly affected. FVIII primarily increased the $k_{cat}$ of FIXa and, as with the antibody-FIXa complex, the effect of FVIII on FIXa was strictly dependent on the presence of $Ca^{2+}$ ions and phospholipids. It could thus be concluded that the conformational change induced by FVIII and our antibodies was similar. The procoagulant antibodies analyzed did not compete with FVIII for FIXa binding, but instead competed with each other. This indicated that few 'hot spots' were responsible for a proper conformational change.

The effector function of the antibodies was confirmed in plasma assays. In contrast to FXa generation assays, plasma assays using model systems that contained purified proteins probed the entire intrinsic coagulation pathway from FXIIa to the formation of thrombin, as well as the inactivation of activated coagulation factors by antithrombin and $a_2$-macroglobulin. The antibodies were effective in plasma assays in a dose-dependent manner until FIX was saturated with antibody. The effectiveness was lower than in the case of FVIII, which was in line with the kinetic data obtained in model systems. The antibody neither affected the other procoagulant reactions nor the inactivation of the activated coagulation factors by plasma protease inhibitors. This conclusion was based upon the observation that thrombin generation curves showed an identical burst and inactivation of thrombin with both antibodies and FVIII. FVIII-like activity was also detected in FVIII-depleted and in FVIII-inhibitor plasma, giving evidence, that inhibitory antibodies directed against FVIII did not affect the activity of procoagulant antibodies.

EXAMPLE 7

Testing Procoagulant Activity of Antibody 224F3 in an in vivo Mouse Model

Materials:

Factor IX knockout mice, males and females, with a body weight above 25 g were used. Human FIX was purchased from Enzyme Research Laboratories (USA). Monoclonal antibody 224F3 (sublone 224 AE3) was prepared as described in Examples 1, 2 and 3. Non-specific polyclonal mouse IgG was purchased from Sigma (USA). FIX, antibody 224F3 and unspecific mouse IgG were diluted to the desired concentration in application-buffer (68 mM NaCl, 100 mM Glycin, 20 mM L-Histidin, pH 7.2+0.1% BSA). FVIII-Inhibitor plasma was developed in goat by multiple injections of human FVIII, harvested by plasmapheresis and was heat-inactivated at 56° C. for 2 hours. The inhibitor plasma showed more than 2000 BU. Normal goat plasma was harvested from a non immunized goat and treated as the inhibitor plasma.

Method:

20 FIX knockout mice were treated with FVIII inhibitor plasma (developed in goat, 20 ml/kg) to achieve an additional FVIII immunodepletion. After one hour, human FIX was injected into the mice (300 U/kg=1500 µg/kg), to overcome FIX depletion. Thus, the mice corresponded to FVIII inhibitor-patients. After 10 minutes, mice were treated with antibody 224F3 (2000 µg/kg). After an additional 10 minutes, a tail clip was performed (1 cm from the end) and bleeding characteristics were determined as described by Turecek et al., Thrombosis and Haemostasis 77 (3), 591-599 (1997).

20 mice were treated with normal goat-plasma (20 ml/kg). After one hour, human FIX (300 U/kg=1500 µg/kg) was injected into the mice. After 10 minutes, mice were treated with buffer without antibody (10 ml/kg). After an additional 10 minutes, a tail clip was performed (1 cm from the end) and bleeding characteristics were determined. These mice served as a positive control group as they displayed FIX activity and FVIII activity and thus had normal bleeding characteristics.

20 FIX knockout mice were treated with FVIII inhibitor plasma (developed in goat, 20 ml/kg) to achieve a additional FVIII immunodepletion. After one hour, human FIX was injected into the mice (300 U/kg=1500 µg/kg), to overcome FIX depletion. Thus, the mice corresponded to FVIII inhibitor-patients. After 10 minutes, mice were treated with non-specific mouse IgG (2000 µg/kg). After an additional 10 minutes, a tail clip was performed (1 cm from the end) and bleeding characteristics were determined. These mice corresponded to FVIII inhibitor patients and were treated with non active antibodies and thus served as a negative control group.

Figure 9:
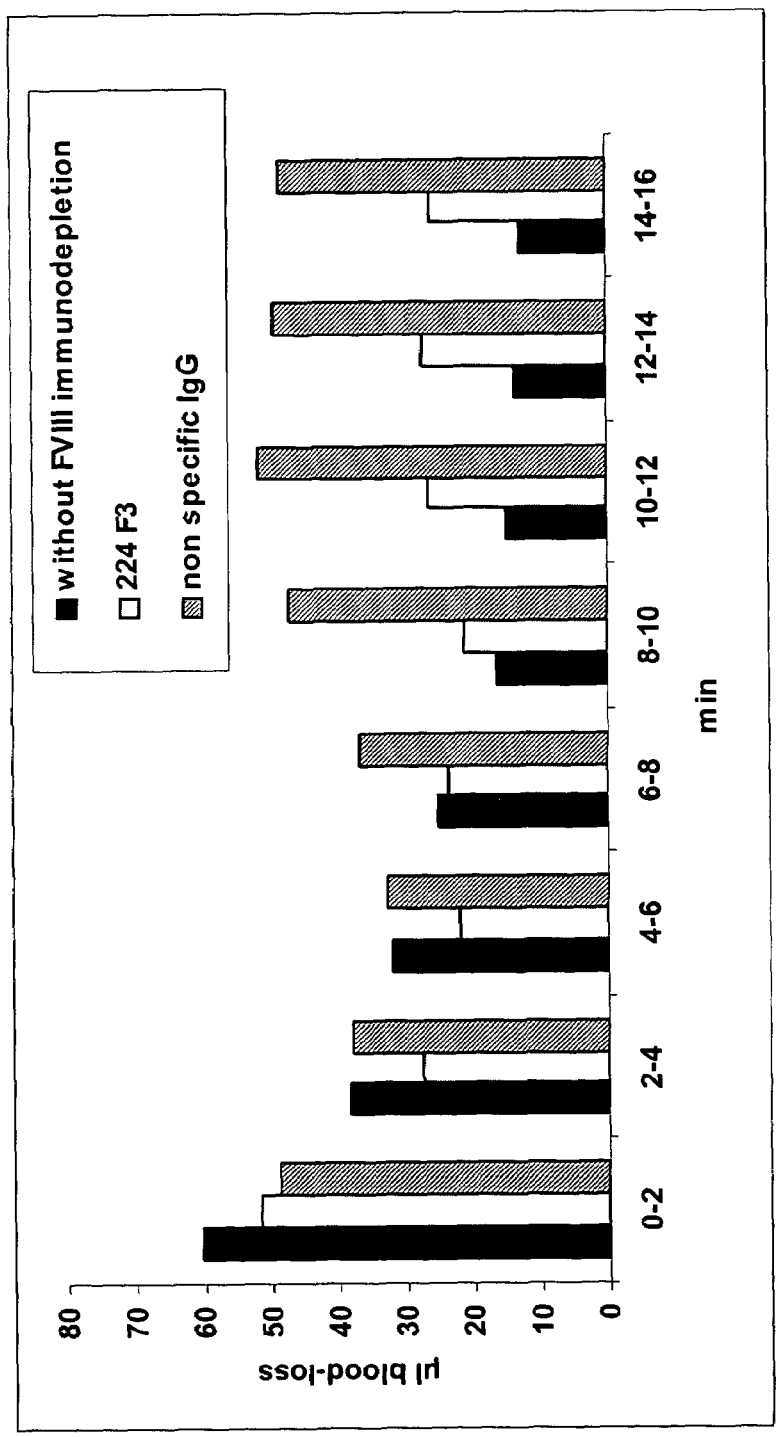
FIG. 9 shows the blood loss in μl (ordinate) as a function of the indicated time interval (abscissa) for FIX knockout mice that were treated with normal goat plasma and human FIX (without immunodepletion, black boxes); with inhibitor plasma, human FIX and antibody 224F3 as ligand (grey boxes); and with inhibitor plasma, human FIX and non specific IgG (hatched boxes).

Results:

Blood loss was determined in each individual mouse every two minutes. The results of the 20 mice of each group were averaged and were displayed in FIG. 9. FIG. 9 showed the blood loss that was observed during the first 16 minutes at each time interval. In the control group that retained full FVIII activity (without FVIII immunodepletion), blood loss was approximately 60 µl in the first two minutes after tail clip. In this control group, blood loss continuously decreased to approximately 15 µl at time internal 14-16 min after tail clip. After immunodepletion of FVIII and treatment with antibody 224F3, blood loss showed a similar characteristic: 50 µl blood loss at the initial two minutes and decrease of blood loss down to approximately 20 µl per time interval (two minutes). This indicated that blood coagulation took place, thus slowing blood loss. In the case of the second control group, the blood loss characteristic of mice, completely devoid of FVIII activity was shown. The initial blood loss again was determined 50 µl, but the decrease in blood loss was not that pronounced and increased after eight minutes.

Figure 10:
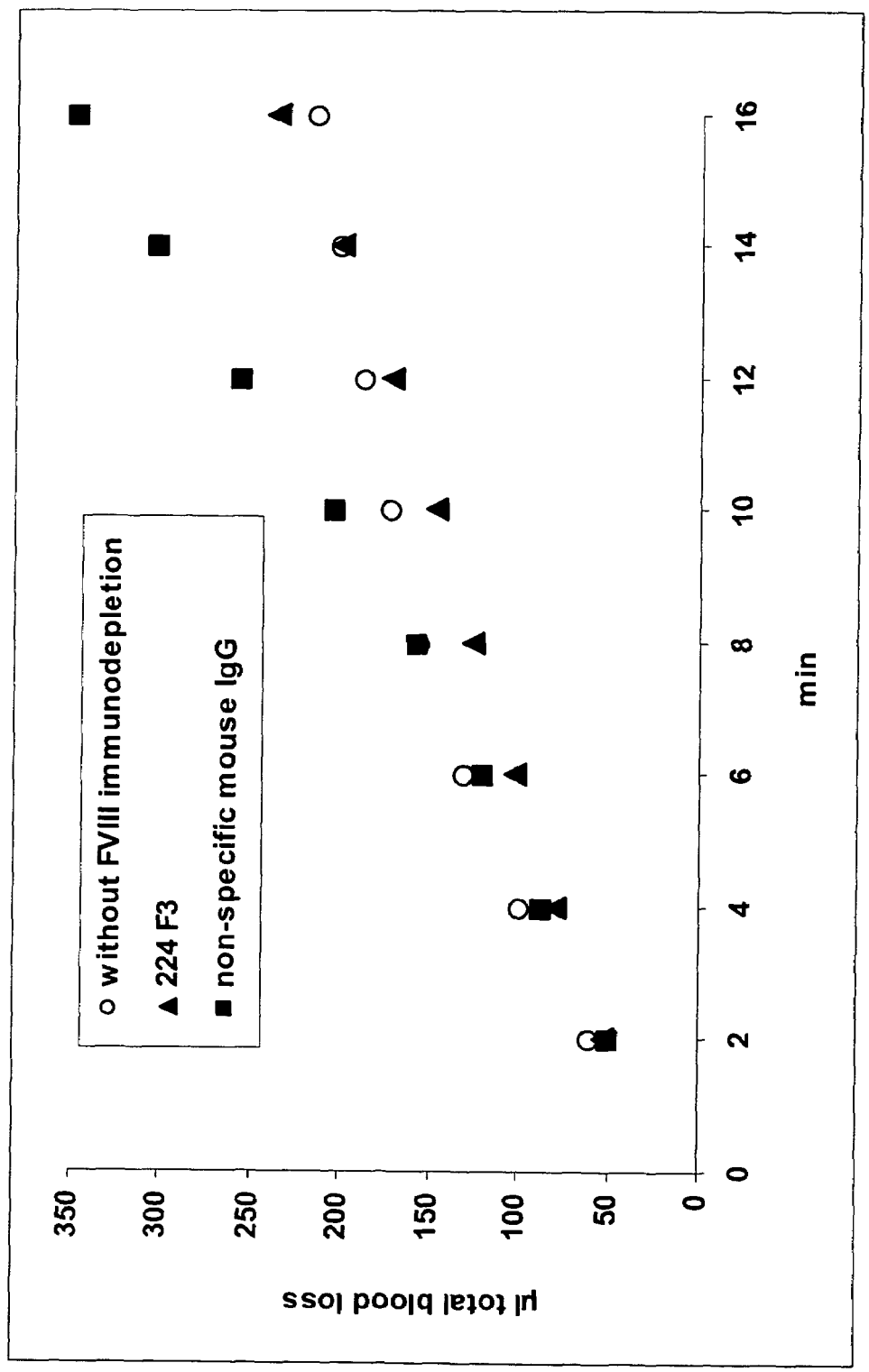
FIG. 10 shows the total blood loss in μl (ordinate) as a function of time for FIX knockout mice that are treated with normal goat plasma and human FIX (without immunodepletion, open circles); with inhibitor plasma, human FIX and antibody 224F3 as ligand (filled triangles); and with inhibitor plasma, human FIX and non specific IgG (filled squares).

FIG. 10 showed the same data; however, the total blood loss was indicated. Blood loss of the group that was treated with non-specific mouse IgG was higher than in the two other groups, reaching a total blood loss of 350 µl after 16 minutes. Mice that were treated with antibody 224F3 or that were not FVIII immunodepleted, showed a similar blood loss characteristic during the initial 16 minutes, with a total blood loss of approximately 220 µl during the first 16 minutes. The blood loss rates within the first 16 minutes of the 20 mice treated with 224F3 and of the 20 mice treated with unspecific mouse IgG (negative control group) were compared applying a Student's t-test. The difference of both groups was found to be statistically significant (p<0.02).

EXAMPLE 8

Development of Derivatives of Antibody 224F3

Principle:

Derivatives of procoagulant antibody 224F3 with potentially enhanced procoagulant activity could be developed, e.g. by introducing mutations into the VL and/or the VH encoding sequence. Preferably such mutations were done using state of the art cloning techniques and a bacterial expression vector, harbouring the VH and VL genes in the scFv format (see, e.g., methods listed in section 11 part C). The following is a list of exemplary mutations that could be introduced: (i) specific mutations into VH and/or VL, (ii) random mutations distributed over the entire sequence of VH and/or VL (e.g. by error prone PCR) or (iii) random mutations within a specific CDR. These mutated derivatives could be pre-selected by the phage display technology, thus enriching scFv variants that were able to bind to human FIXa. The variants could be expressed into the supernatant using standard expression techniques and could be screened for FVIII like activity using, for example, the following assay:

Fluorescence Assay for Determination of FIXa Activating Potential of Antibody Fragments Containing a Hexa-histidine (SEQ ID NO:12) Tag:

Materials:

Buffers:
  TBS: 25 mM Tris; 150 mM NaCl pH 7,5
  TBS/2% BSA: 2 g BSA/ 100 ml TBS
  HNa: 25 mM HEPES, 175 mM NaCl, pH 7.35
  HNaBSA5: 5 mg BSA/ml HNa-Puffer Reagents:
  Penta-HIS antibody, BSA free (Qiagen)
  hFIXaβ (ERL)
  hFX(ERL)
  Phospholipids:
  Fluorogenic substrate Pefafluor FXa: $CH_3So_2$-D-CHA-Gly-Arg-AMC.AcOH (Pentapharm LTD)
PL/Ca++/hFX/fluorogenic substrate-mix: Final concentration: 4.3mM $CaCl_2$; 9.4 μM PL; 29.3 nM hFX; 167 μM fluorogenic substrate Method:

The wells of a microtiter plate were coated with 2 μg/ml Penta-HIS antibody and were blocked with TBS/2% BSA afterwards. Bacterial supernatant containing the expressed variants of 224F3 (e.g. scFv format) were diluted in TBS/2% BSA and incubated in the wells. The plate was washed and incubated with human FIXa (1 μg/ml, diluted in HNaBSA5). After washing, the PL/$Ca^{++}$/hFX/fluorogenic substrate-mix was applied. The generation of fluorescence signal was measured in a fluorescence reader. When a scFv with FVIII like activity was immobilized on the well, enhanced FXa generation and an accelerated generation of fluorescence signal could be observed.

Examples of Derivatives of Antibody 224F3:

Applying the above described method, several mutated versions of 224F3 were constructed and analysed for binding to FIXaβ by an ELISA and for FVIII-like activity by the fluorescence assay. Table 2 showed which point mutations were constructed and if the mutation influenced the binding and/or FIXa activating potential of the antibody. In particular, this table showed specific mutations introduced into 224F3-scFv and the results of subsequent testing for FIXaβ-binding (ELISA) and FIXa activating potential (fluorescence assay). Activity similar to the wild type scFv was indicated by (+); activity significantly lower than activity of wild type was indicated by a (−). With respect to nomenclature, S31I, for instance, meant that amino acid no. 31 (serine, S) of the heavy chain (within H1-loop) was replaced by an I (isoleucine).

TABLE 2

| | ELISA | fluorescence assay | influence of mutation |
|---|---|---|---|
| wild type 224F3-scFv | + | + | |
| S31I (H1-loop) | + | − | yes |
| F52A (H2-Loop) | + | + | no |
| D55A (H2-Loop) | + | + | no |
| S57Y (H2-Loop) | + | + | no |
| K59A (H2-Loop) | + | + | no |
| R103A (H3-Loop) | + | + | no |
| D105A (H3-Loop) | + | + | no |
| Y108A (H3-Loop) | − | − | yes |
| Y110A (H3-Loop) | + | + | no |
| S27I (L1-Loop) | + | + | no |
| S30I (L1-Loop) | − | − | yes |
| S92I (L3-Loop) | + | + | no |
| Y93A (L3-Loop) | − | − | yes |

All publications, sequences of accession numbers, and patent applications cited in this specification are herein incorporated by reference as if each individual publication or patent application were specifically and individually indicated to be incorporated by reference.

What is claimed is:

1. An isolated antibody comprising
   a $V_H$ domain having a CDR1 comprising the sequence set forth in SEQ ID NO:6, a CDR2 comprising the sequence set forth in SEQ ID NO:7, and a CDR3 comprising the sequence set forth in SEQ ID NO:8; and
   a $V_L$ domain having a CDR1 comprising the sequence set forth in SEQ ID NO:3, a CDR2 comprising the sequence set forth in SEQ ID NO:4, and a CDR3 comprising the sequence set forth in SEQ ID NO:5,
   wherein the antibody can bind to Factor IX/Factor IXa and increase the procoagulation activity of Factor IXa.

2. The isolated antibody according to claim 1, wherein the $V_H$ domain comprises the sequence set forth in SEQ ID NO:1 and
   the $V_L$ domain comprises the sequence set forth in SEQ ID NO:2.

3. The isolated antibody according to claim 1, wherein the antibody is an IgG.

4. The isolated antibody according to claim 1, wherein the antibody is monoclonal.

5. The isolated antibody according to claim 1, wherein the antibody is an antibody fragment.

6. The isolated antibody according to claim 1, wherein the antibody is a recombinant antibody.

7. The isolated antibody according to claim 6, wherein the antibody is a single chain antibody.

8. The isolated antibody according to claim 1, wherein the antibody is a humanized antibody.

9. The isolated antibody of claim 1, wherein the antibody is labeled.

10. A pharmaceutical composition comprising the isolated antibody of claim 1 and a pharmaceutically acceptable carrier and/or diluent.

11. The pharmaceutical composition comprising the isolated antibody of claim 2.

12. The pharmaceutical composition according to claim 11, further comprising a Factor selected from the group consisting of Factor IX, Factor IXaα, Factor IXaβ, and combinations thereof.

13. The pharmaceutical composition according to claim 10, further comprising a Factor selected from the group consisting of Factor IX, Factor IXaα, Factor IXaβ, and combinations thereof.

* * * * *